United States Patent
Takami et al.

(10) Patent No.: US 11,439,456 B2
(45) Date of Patent: *Sep. 13, 2022

(54) ENERGY SOURCE APPARATUS

(71) Applicant: Olympus Corporation, Hachioji (JP)

(72) Inventors: Sadayoshi Takami, Hachioji (JP);
Tsuyoshi Hayashida, Hachioji (JP);
Tsunetaka Akagane, Hachioji (JP);
Kazue Tanaka, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 351 days.

This patent is subject to a terminal disclaimer.

(21) Appl. No.: 16/568,614

(22) Filed: Sep. 12, 2019

(65) Prior Publication Data
US 2020/0000508 A1    Jan. 2, 2020

Related U.S. Application Data

(63) Continuation of application No. PCT/JP2017/010455, filed on Mar. 15, 2017.

(51) Int. Cl.
*A61B 18/12*    (2006.01)
*A61B 18/14*    (2006.01)
*A61B 18/00*    (2006.01)

(52) U.S. Cl.
CPC .......... *A61B 18/1206* (2013.01); *A61B 18/14* (2013.01); *A61B 2018/0016* (2013.01); *A61B 2018/126* (2013.01)

(58) Field of Classification Search
CPC ................ A61B 18/1206; A61B 18/14; A61B 2018/0016; A61B 2018/126;
(Continued)

(56) References Cited

U.S. PATENT DOCUMENTS 5,496,312 A * 3/1996 Klicek .............. A61B 18/1206
606/34
5,558,671 A * 9/1996 Yates .............. A61B 17/07207
606/38

(Continued)

FOREIGN PATENT DOCUMENTS

DE        69630530 T2 *  8/2004   ......... A61B 18/1815
JP        2009247893       10/2009
(Continued)

OTHER PUBLICATIONS

International Search Report and Written Opinion from corresponding International Application No. PCT/JP2017/010455, dated Jun. 13, 2017.

*Primary Examiner* — Joseph A Stoklosa
*Assistant Examiner* — Nancy K Sloan
(74) *Attorney, Agent, or Firm* — Oliff PLC

(57) ABSTRACT

A treatment system includes a treatment tool and an energy source apparatus used to supply electrical energy to the treatment tool. The treatment tool includes a heater and bipolar electrodes to grip a treatment target. The energy source apparatus includes a processor to control the output to the bipolar electrodes and the heater, respectively. The processor directs the output to the bipolar electrodes and detects an initial value of the impedance of the treatment target. The processor determines whether or not the impedance has reached a minimum value and then retrieves a parameter that is detected before the minimum value of the impedance is detected. The processor performs a first process and/or a second process based on the acquired parameter after the minimum value is detected. The first process determines whether or not the output to the heater is required. The second process sets a target value.

13 Claims, 8 Drawing Sheets

(58) Field of Classification Search
CPC ........... A61B 2018/00761; A61B 2018/00702;
A61B 2018/00642; A61B 2018/00672;
A61B 2018/00875; A61B 2018/00791;
A61B 2018/0063; A61B 2018/00589;
A61B 2018/00404; A61B 2018/00994;
A61B 18/1445; A61B 18/085; A61B
18/10; A61B 18/12; C23C 14/0063
See application file for complete search history.

(56) References Cited

U.S. PATENT DOCUMENTS

| | | | | |
|---|---|---|---|---|
| 5,957,920 A * | 9/1999 | Baker | ............... | A61B 18/1485 607/101 |
| 6,053,937 A * | 4/2000 | Edwards | ............ | A61B 18/1482 606/41 |
| 6,197,022 B1 * | 3/2001 | Baker | ............... | A61B 18/1485 606/41 |
| 6,312,426 B1 * | 11/2001 | Goldberg | ........... | A61B 18/1445 606/51 |
| 6,312,428 B1 * | 11/2001 | Eggers | ................ | A61B 5/0531 606/41 |
| 6,402,742 B1 * | 6/2002 | Blewett | .............. | A61B 18/1477 607/101 |
| 6,409,722 B1 * | 6/2002 | Hoey | ................ | A61B 18/1206 606/41 |
| 6,416,509 B1 * | 7/2002 | Goble | ................. | A61B 18/082 606/37 |
| 6,551,311 B2 * | 4/2003 | Lee | ........................ | A61B 18/18 606/41 |
| 6,564,806 B1 * | 5/2003 | Fogarty | ................. | A61B 90/39 606/116 |
| 6,632,221 B1 * | 10/2003 | Edwards | ............ | A61B 18/1815 606/41 |
| 6,682,501 B1 * | 1/2004 | Nelson | .................. | A61B 5/415 604/22 |
| 6,775,575 B2 * | 8/2004 | Bommannan | ...... | A61B 18/1445 607/101 |
| 6,855,142 B2 * | 2/2005 | Harano | .............. | A61B 18/1206 128/898 |
| 6,962,587 B2 * | 11/2005 | Johnson | ................ | A61B 18/18 606/41 |
| 7,329,257 B2 * | 2/2008 | Kanehira | ........... | A61B 17/3201 606/45 |
| 7,341,586 B2 * | 3/2008 | Daniel | ............... | A61B 18/1477 606/41 |
| 7,344,533 B2 * | 3/2008 | Pearson | ............ | A61B 18/1477 606/41 |
| 7,419,487 B2 * | 9/2008 | Johnson | ............ | A61B 18/1477 606/41 |
| 7,862,565 B2 * | 1/2011 | Eder | ................... | A61B 18/1442 606/41 |
| 8,321,019 B2 * | 11/2012 | Esch | ...................... | A61B 18/08 607/27 |
| 8,562,602 B2 * | 10/2013 | Azure | .................... | A61B 18/18 606/42 |
| 9,031,667 B2 * | 5/2015 | Williams | ........... | A61N 1/36021 607/101 |
| 9,119,619 B2 * | 9/2015 | Honda | ............... | A61B 18/1442 |
| 9,125,663 B2 * | 9/2015 | Ichikawa | ............. | A61B 18/085 |
| 9,198,710 B2 * | 12/2015 | Honda | ................. | A61B 18/085 |
| 9,204,992 B2 * | 12/2015 | Honda | .................... | A61F 7/007 |
| 9,241,762 B2 * | 1/2016 | Podhajsky | ............. | A61B 18/14 |
| 9,414,882 B2 * | 8/2016 | Tanaka | ................... | A61B 18/10 |
| 9,603,654 B2 * | 3/2017 | Azure | ................ | A61B 18/1477 |
| 9,622,813 B2 * | 4/2017 | Krugman | .............. | A61B 6/032 |
| 11,129,982 B2 * | 9/2021 | Iger | ..................... | A61B 18/1402 |
| 2002/0052601 A1 * | 5/2002 | Goldberg | ............ | A61B 18/1445 606/41 |
| 2003/0073987 A1 * | 4/2003 | Sakurai | ............... | A61B 18/1442 606/28 |
| 2006/0100620 A1 * | 5/2006 | Daniel | ............... | A61B 18/1477 606/49 |
| 2006/0167445 A1 * | 7/2006 | Shafirstein | ............. | A61B 18/20 606/28 |
| 2008/0125775 A1 * | 5/2008 | Morris | ............... | A61B 18/1477 606/50 |
| 2008/0262490 A1 * | 10/2008 | Williams | ............... | A61N 1/403 606/34 |
| 2008/0275440 A1 * | 11/2008 | Kratoska | ............ | A61B 18/1477 606/41 |
| 2009/0076499 A1 * | 3/2009 | Azure | ..................... | A61B 18/14 606/41 |
| 2009/0204114 A1 * | 8/2009 | Odom | ................... | A61B 18/1445 606/51 |
| 2009/0248002 A1 | 10/2009 | Takashino et al. | | |
| 2011/0301590 A1 * | 12/2011 | Podhajsky | ......... | A61B 18/1815 606/34 |
| 2012/0136354 A1 | 5/2012 | Rupp | | |
| 2012/0150169 A1 * | 6/2012 | Zielinksi | ............. | A61B 18/1492 606/34 |
| 2013/0282084 A1 * | 10/2013 | Mathur | ............... | A61B 18/1492 607/101 |
| 2013/0338656 A1 | 12/2013 | Irisawa et al. | | |
| 2015/0196351 A1 * | 7/2015 | Stone | ....................... | A61N 1/32 606/41 |
| 2016/0066978 A1 | 3/2016 | Keller et al. | | |
| 2016/0113709 A1 * | 4/2016 | Maor | ................. | A61B 18/1492 606/41 |
| 2016/0143684 A1 | 5/2016 | Honda et al. | | |
| 2016/0184006 A1 * | 6/2016 | Azure | ..................... | A61N 1/06 606/41 |
| 2016/0242836 A1 * | 8/2016 | Eggers | ................ | A61B 18/149 |
| 2017/0065330 A1 * | 3/2017 | Mickelsen | ............. | A61B 17/08 |
| 2017/0224407 A1 * | 8/2017 | Takami | ............. | A61B 18/10 |
| 2018/0042662 A1 * | 2/2018 | Legaspi | ............. | A61B 18/12 |
| 2018/0296265 A1 * | 10/2018 | Hasegawa | ............. | A61B 18/10 |
| 2020/0237426 A1 * | 7/2020 | Miller | ................ | A61B 18/1206 |

FOREIGN PATENT DOCUMENTS

| | | |
|---|---|---|
| JP | 2012115669 | 6/2012 |
| JP | 2016041317 | 3/2016 |
| JP | 2016055172 | 4/2016 |
| WO | 2013088891 | 6/2013 |

* cited by examiner

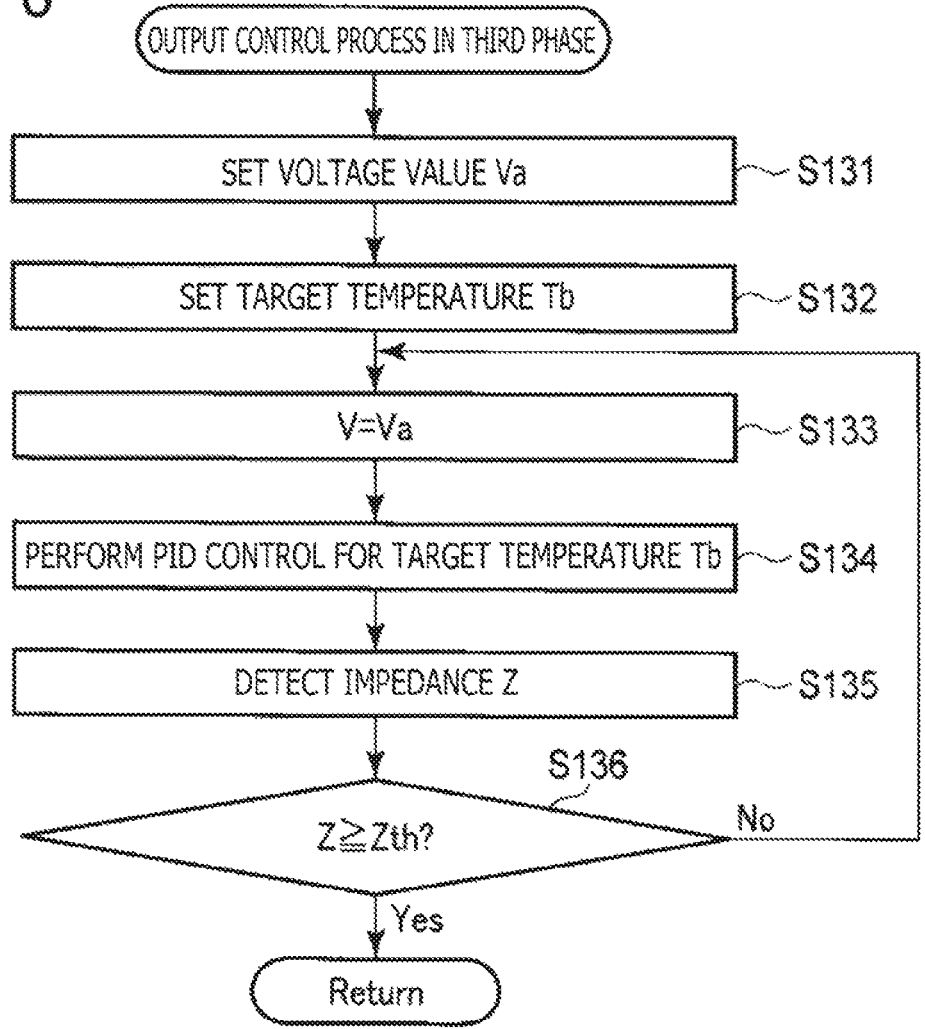
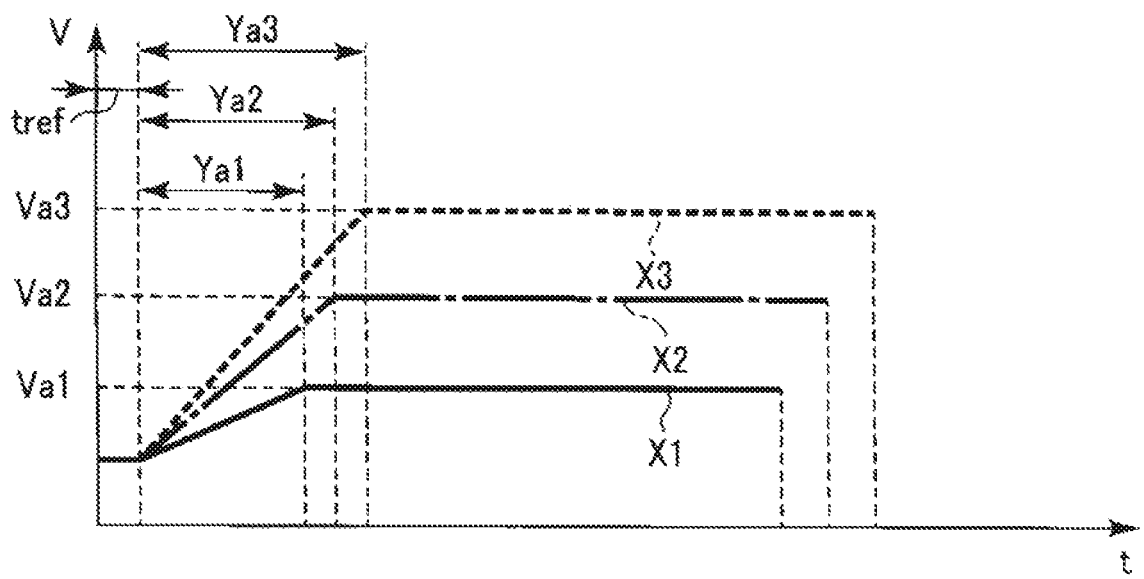

ENERGY SOURCE APPARATUS

CROSS-REFERENCE TO RELATED APPLICATION

This application is a continuation application of PCT Application No. PCT/JP 2017/010455 filed on Mar. 15, 2017, which is hereby incorporated by reference in its entirety.

TECHNICAL FIELD

The disclosed technology relates generally to an energy source apparatus, and more particularly, some embodiments relate to an energy source apparatus for use with a treatment tool having bipolar electrodes and a heater.

DESCRIPTION OF THE RELATED ART

US Patent Application Pub. No. 2009/0248002A1 discloses a treatment tool capable of gripping a treatment target such as a biotissue or the like between a pair of grippers and an energy source apparatus for supplying the treatment tool with electric energy. In the treatment tool, each of the grippers includes an electrode and one of the grippers includes a heater. The energy source apparatus outputs high-frequency electric power to the electrodes, i.e., bipolar electrodes, and outputs heater electric power to the heater. Consequently, a high-frequency current flows between the electrodes through the gripped treatment target and heat generated by the heater is applied to the gripped treatment target. In other words, both the high-frequency current and the heater heat are applied to the treatment target.

As disclosed in US Pub. No. 2009/0248002A1, a treatment using a treatment tool that applies both a high-frequency current and heater heat to a treatment target may modify the treatment target by applying the high-frequency current, the heater heat, etc. thereto, sealing or coagulating the treatment target. In this case, while the high-frequency current, the heater heat, etc. are being applied to the treatment target, the water in the treatment target is boiled until the treatment target is dehydrated and dried. In the treatment that seals or coagulates the treatment target, the longer the time in which the water in the treatment target is boiled, the longer the time in which the treatment target is welded, i.e., the time in which the treatment target is fused, increasing the ability to seal and coagulate the treatment target. Therefore, in the treatment that seals or coagulates the treatment target, it is required to control the output from a heater power supply to a heater depending on the state of the treatment target so that the time to weld the treatment target will be increased.

BRIEF SUMMARY OF EMBODIMENTS

The disclosed technology has been made in view of the foregoing.

One aspect of the disclosed technology is directed to an energy source apparatus of a treatment tool having a heater and bipolar electrodes attached to one another. The energy source apparatus includes an energy output source that outputs high-frequency electric power to the bipolar electrodes so as to cause a high-frequency current to flow through a treatment target between the bipolar electrodes and outputs heater electric power to the heater so as to cause the heater to generate heat. A processor controls the output to the bipolar electrodes and the output to the heater. The processor directs the output to the bipolar electrodes and detects an initial value of the impedance of the treatment target. The processor determines whether or not the impedance has reached a minimum value. The processor retrieves a parameter that is detected before the minimum value of the impedance is detected and the parameter is related to the impedance and/or the output to the bipolar electrodes. The processor performs a first process and/or a second process based on the acquired parameter after the minimum value is detected. The first process determining whether or not the output to the heater is required, the second process setting a target value, the target value is related to an output control process for controlling the output to the heater.

Another aspect of the disclosed technology is directed to a treatment system having a treatment tool and an energy source apparatus. The treatment tool includes a heater and bipolar electrodes to grip a treatment target and the energy source apparatus is used to supply electrical energy to the treatment tool. The energy output source is configured to output high-frequency electric power to the bipolar electrodes so as to cause a high-frequency current to flow through a treatment target between the bipolar electrodes and outputs heater electric power to the heater so as to cause the heater to generate heat. A processor controls the output to the bipolar electrodes and the heater, respectively. The processor directs the output to the bipolar electrodes and detects an initial value of the impedance of the treatment target. Next, the processor determines whether or not the impedance has reached a minimum value and retrieves a parameter that is detected before the minimum value of the impedance is detected. The parameter is related to the impedance and/or the output to the bipolar electrodes. Finally, the processor performs a first process and/or a second process based on the acquired parameter after the minimum value is detected, the first process determines whether or not the output to the heater is required, the second process sets a target value, the target value being related to an output control process for controlling the output to the heater.

A further aspect of the disclosed technology is directed to a method of operating a treatment system having a treatment tool including a heater and bipolar electrodes to grip a treatment target and an energy source apparatus used to supply electrical energy to the treatment tool. The energy source apparatus includes at least one processor to control the output to the bipolar electrodes and the heater, respectively. The at least one processor: directing the output to the bipolar electrodes and detecting an initial value of the impedance of the treatment target; determining whether or not the impedance has reached a minimum value; retrieving a parameter that is detected before the minimum value of the impedance is detected, the parameter being related to the impedance and/or the output to the bipolar electrodes; and performing a first process and/or a second process based on the acquired parameter after the minimum value is detected, the first process determining whether or not the output to the heater is required, the second process setting a target value, the target value being related to an output control process for controlling the output to the heater.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 6 is a flowchart of a processing sequence carried out by the processor according to the first embodiment in an output control process in a third phase.

FIG. 7 is a schematic diagram illustrating an example of target trajectories for an output voltage from a high-frequency power supply in the processing sequence carried out by the processor according to the first embodiment.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of the present disclosure to provide an energy source apparatus that appropriately controls the output from a heater power supply based on the state of a treatment target for thereby increasing the ability to seal and coagulate the treatment target.

First Embodiment

A first embodiment of the disclosed technology will be described below with reference to FIGS. 1 through 9.

Figure 1:
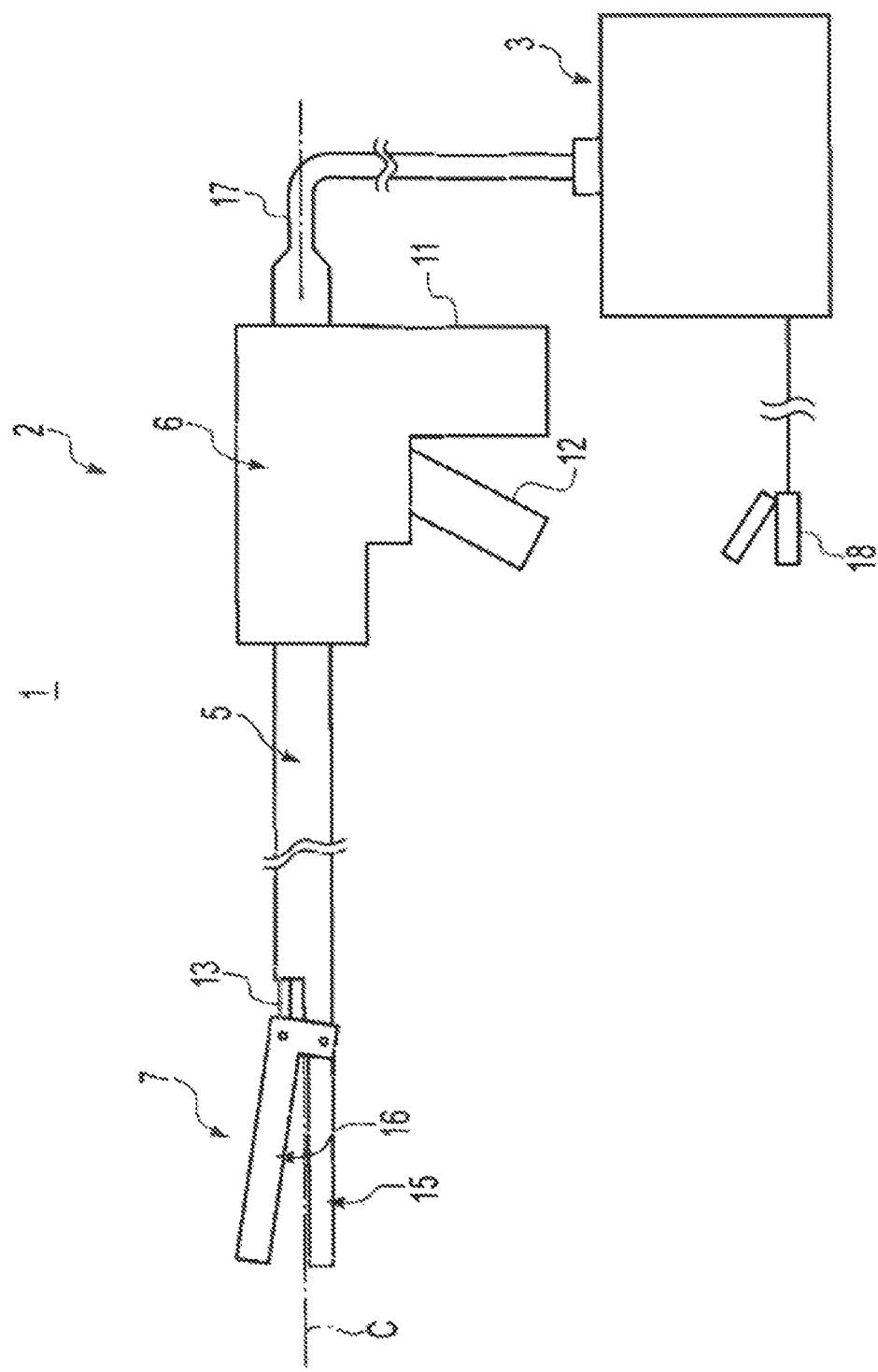
FIG. 1 is a schematic view illustrating a treatment system according to a first embodiment.

FIG. 1 is a view illustrating a treatment system 1 according to the present embodiment. As illustrated in FIG. 1, the treatment system 1 includes a treatment tool 2 and an energy source apparatus 3 for supplying the treatment tool 2 with electric energy. When the treatment tool 2 is in use, the energy source apparatus 3 is used together with the treatment tool 2. The treatment tool 2 includes a shaft 5 having a longitudinal axis C as its central axis. A housing 6 that can be held is coupled to an end, i.e., proximal end, of the shaft 5 in a direction along the longitudinal axis C. An end effector 7 is disposed on the end of the shaft 5 that is opposite to the end where the housing 6 is positioned, i.e., on a distal end of the shaft 5. The housing 6 includes a grip 11 and a handle 12 mounted angularly movably thereon. When the handle 12 is angularly moved with respect to the housing 6, the handle 12 is opened or closed with respect to the grip 11.

The end effector 7 includes a pair of grippers 15 and 16. In the treatment tool 2, a movable member 13 extends along the longitudinal axis C inside or outside of the shaft 5. The movable member 13 has an end, i.e., distal end, connected to the end effector 7. The other end, i.e., proximal end, of the movable member 13 is coupled to the handle 12 in the housing 6. When the handle 12 is opened or closed with respect to the grip 11, the movable member 13 moves along the longitudinal axis C of the shaft 5, opening or closing the grippers 15 and 16. The grippers 15 and 16 are thus capable of gripping a biotissue such as a blood vessel or the like as a treatment target therebetween. According to an embodiment, one of the grippers 15 and 16 is integral with or fixed to the shaft 5, whereas the other of the grippers 15 and 16 is angularly movably mounted on a distal end of the shaft 5. According to another embodiment, both the grippers 15 and 16 are angularly movably mounted on the distal end of the shaft 5. According to an embodiment, an operating member, not illustrated, such as a rotary knob or the like, is mounted on the housing 6. When the operating member is rotated with respect to the housing 6, the shaft 5 and the end effector 7 are rotated about the longitudinal axis C with respect to the housing 6.

A cable 17 has an end connected to the housing 6. The other end of the cable 17 is separably connected to the energy source apparatus 3. The treatment system 1 includes a foot switch 18 as an operating member separate from the treatment tool 2. The foot switch 18 is electrically connected to the energy source apparatus 3. The foot switch 18 inputs an operation for causing the energy source apparatus 3 to output electric energy to the treatment tool 2. According to an embodiment, an operating button or the like that is mounted as an operating member on the housing 6 is included instead of or in addition to the foot switch 18. The energy source apparatus 3 outputs electric energy to the treatment tool 2 in response to an operation entered through the operating member.

Figure 2:
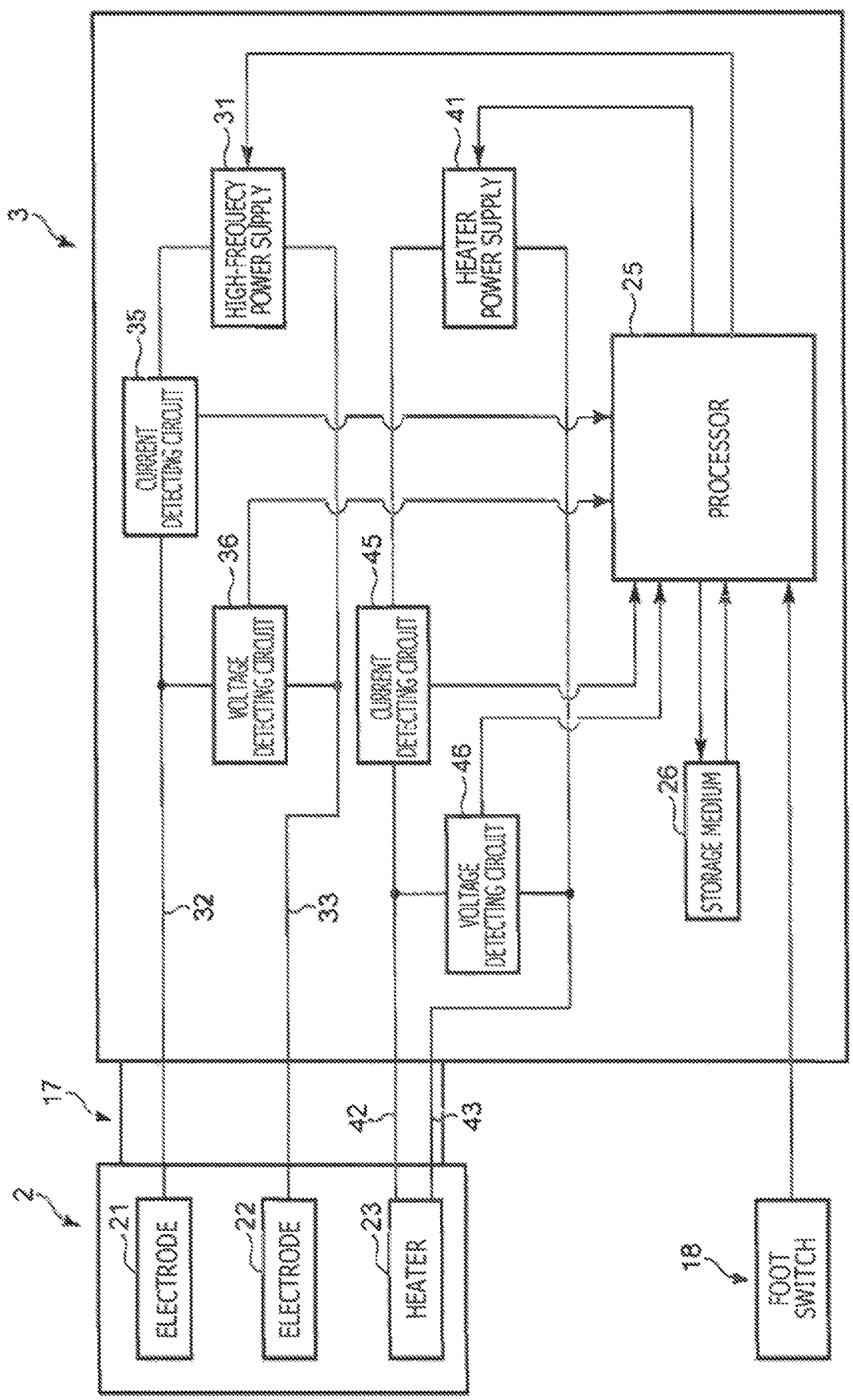
FIG. 2 is a block diagram schematically illustrating an arrangement for supplying electric energy from an energy source apparatus according to the first embodiment to a treatment tool.

FIG. 2 is a diagram illustrating an arrangement for supplying electric energy, i.e., high-frequency electric power P and heater electric power P' to be described hereinafter according to the present embodiment, from the energy source apparatus 3 to the treatment tool 2. As illustrated in FIG. 2, the treatment tool 2 includes an electrode 21 on the gripper 15 and an electrode 22 on the gripper 16. The electrodes 21 and 22 are bipolar electrodes included in the end effector 7. The end effector 7 includes a heater 23 as a heat generating element disposed on at least one of the grippers 15 and 16.

The energy source apparatus 3 includes a processor 25, i.e., controller and a storage medium 26. The processor 25 is in the form of an integrated circuit or the like including a central processing unit (CPU), an application specific integrated circuit (ASIC), a field programmable gate array (FPGA), or the like. The energy source apparatus 3 may include only one processor 25 or a plurality of processors 25. The processor 25 carries out a processing sequence according to programs stored in the processor 25 or the storage medium 26. The storage medium 26 stores processing programs used by the processor 25, parameters, functions, and tables used in operations performed by the processor 25, and so on. The processor 25 detects whether or not an operation is entered through the operating member such as the foot switch 18 or the like.

The energy source apparatus 3 includes a high-frequency power supply 31 as an energy output source. The high-frequency power supply 31 includes a waveform generator, a converting circuit, a transformer, and so on. The high-frequency power supply 31 converts electric power from a battery power supply, an outlet power supply, or the like into high-frequency electric power P. The high-frequency power supply 31 is electrically connected to the electrode 21 on the gripper 15 through an electric supply path 32. The high-frequency power supply 31 is also electrically connected to the electrode 22 on the griper 16 through an electric supply path 33. Each of the electric supply paths 32 and 33 extends in the cable 17, the housing 6, and the shaft 5. Each of the electric supply paths 32 and 33 is in the form of an electric wire or the like. The high-frequency power supply 31 is capable of outputting the converted high-frequency electric power P. While the treatment target is being gripped between the grippers 15 and 16, the high-frequency electric power P output from the high-frequency power supply 31 is supplied through the electric supply paths 32 and 33 to the electrodes 21 and 22. Therefore, a high-frequency current flows through the treatment target between the electrodes, i.e., bipolar electrodes 21 and 22. At this time, the electrodes 21 and 22 have respective potentials that are different from each other. When a high-frequency current having a certain magnitude is applied as treatment energy to the treatment target, the treatment target is modified by the heat caused by the high-frequency current. When an operation is entered through the foot switch 18 or the like, the processor 25 controls the output from the high-frequency power supply 31 to the electrodes 21 and 22 in a manner to be described hereinafter.

The electric paths through which the high-frequency electric power P is output from the high-frequency power supply 31 to the electrodes 21 and 22 include a current detecting circuit 35 and a voltage detecting circuit 36. While the high-frequency electric power P is being output from the high-frequency power supply 31, the current detecting circuit 35 detects the current value of an output current I from the high-frequency power supply 31. At the same time, the voltage detecting circuit 36 detects the voltage value of an output voltage V from the high-frequency power supply 31. An analog signal representing the current value detected by the current detecting circuit 35 and an analog signal representing the voltage value detected by the voltage detecting circuit 36 are converted into digital signals by analog-digital (A/D) converters, not illustrated, or the like. The converted digital signals are transmitted to the processor 25. The processor 25 now acquires information regarding the output current I and the output voltage V from the high-frequency power supply 31. Based on the output current I and the output voltage V that have been acquired, the processor 25 detects impedances of the electric paths through which the high-frequency electric power P is output from the high-frequency power supply 31 to the electrodes 21 and 22.

Based on the impedances of the electric paths for the high-frequency electric power P, the processor 25 detects an impedance Z of the gripped treatment target, i.e., a tissue impedance. Based on the output current I and the output voltage V that have been acquired, the processor 25 also detects an electric power value of the high-frequency electric power P, i.e., an electric power value of the output electric power from the high-frequency power supply 31 to the electrodes 21 and 22. The processor 25 controls the output from the high-frequency power supply 31 and a heater power supply 41 using the output current I and the output voltage V that have been acquired, and the impedance Z and the high-frequency electric power P that have been detected, in a manner to be described hereinafter.

The energy source apparatus 3 includes a heater power supply 41 as an energy output source. The heater power supply 41 includes a converting circuit, a transformer, and so on. The heater power supply 41 converts electric power from a battery power supply, an outlet power supply, or the like into heater electric power P'. The heater power supply 41 is electrically connected to the heater 23 through electric supply paths 42 and 43. Each of the electric supply paths 42 and 43 extends in the cable 17, the housing 6, and the shaft 5. Each of the electric supply paths 42 and 43 is in the form of an electric wire or the like. The heater power supply 41 is capable of outputting the converted heater electric power P'. The heater electric power P' that is output is direct current (DC) electric power or alternate current (AC) electric power. When the heater electric power P' output from the heater power supply 41 is supplied through the electric supply paths 42 and 43 to the heater 23, the heater 23 generates heat. While the treatment target is being gripped between the grippers 15 and 16, the heat generated by the heater 23 is applied to the treatment target. When a certain amount of heater heat is applied as treatment energy to the treatment target, the treatment target is modified, sealed and coagulated. When a large amount of heater heat is applied to the treatment target, the treatment target is incised. When an operation is entered through the foot switch 18 or the like, the processor 25 controls the output from the heater power supply 41 to the heater 23 in a manner to be described hereinafter.

The electric paths through which the heater electric power P' is output from the heater power supply 41 to the heater 23 include a current detecting circuit 45 and a voltage detecting circuit 46. While the heater electric power P' is being output from the heater power supply 41, the current detecting circuit 45 detects the current value of an output current I' from the heater power supply 41. At the same time, the voltage detecting circuit 46 detects the voltage value of an output voltage V' from the heater power supply 41. An analog signal representing the current value detected by the current detecting circuit 45 and an analog signal representing the voltage value detected by the voltage detecting circuit 46 are converted into digital signals by A/D converters, not illustrated, or the like. The converted digital signals are transmitted to the processor 25. The processor 25 now acquires information regarding the output current I' and the output voltage V' from the heater power supply 41. Based on the output current I' and the output voltage V' that have been acquired, the processor 25 detects impedances of the electric paths through which the heater electric power P' is output from the heater power supply 41 to the heater 23. Based on the impedances of the electric paths for the heater power P', the processor 25 detects a resistance R of the heater 23. The resistance R of the heater 23 varies depending on a temperature T of the heater 23. The storage medium 26 or the like stores a function, a table, or the like that represents the relationship between the temperature T and the resistance R of the heater 23. Based on the detected resistance R and the stored relationship between the temperature T and the resistance R, the processor 25 detects the temperature T of the heater 23. Based on the output current I' and the output voltage V' that have been acquired, the processor 25 also detects an electric power value of the heater electric power P', i.e., an electric power value of the output electric power from the heater power supply 41 to the heater 23. The processor 25 controls the output from the heater power supply 41 using the output current I' and the output voltage V' that have been acquired and the temperature T, i.e., the resistance R, and the heater electric power P' that have been detected, in a manner to be described hereinafter.

Next, operation and advantages of the energy source apparatus 3 and the treatment system 1 will be described below. For performing a treatment using the treatment system 1, the treatment tool 2 is connected through the cable 17 to the energy source apparatus 3. The surgeon holds the housing 6 and inserts the end effector 7 into a body cavity such as an abdominal cavity or the like. While a treatment target such as a biotissue or the like is being positioned between the grippers 15 and 16, the surgeon closes the handle 12 on the grip 11. The grippers 15 and 16 are now closed, gripping the treatment target therebetween. When the surgeon enters an operation through the operating member such as the foot switch 18 or the like while the treatment target is being gripped, the output from the high-frequency power supply 31 to the electrodes 21 and 22 and the output from the heater power supply 41 to the heater 23 are controlled. When the high-frequency electric power P is supplied to the electrodes 21 and 22, a high-frequency current flows through the treatment target as described hereinbefore. When the heater electric power P' is supplied to the heater 23, heat generated by the heater 23 is applied to the treatment target. The treatment target is treating using the high-frequency current and the heater heat as treatment energy. In this embodiment, the treatment target is sealed and coagulated by the high-frequency current and the heater heat.

Figure 3:
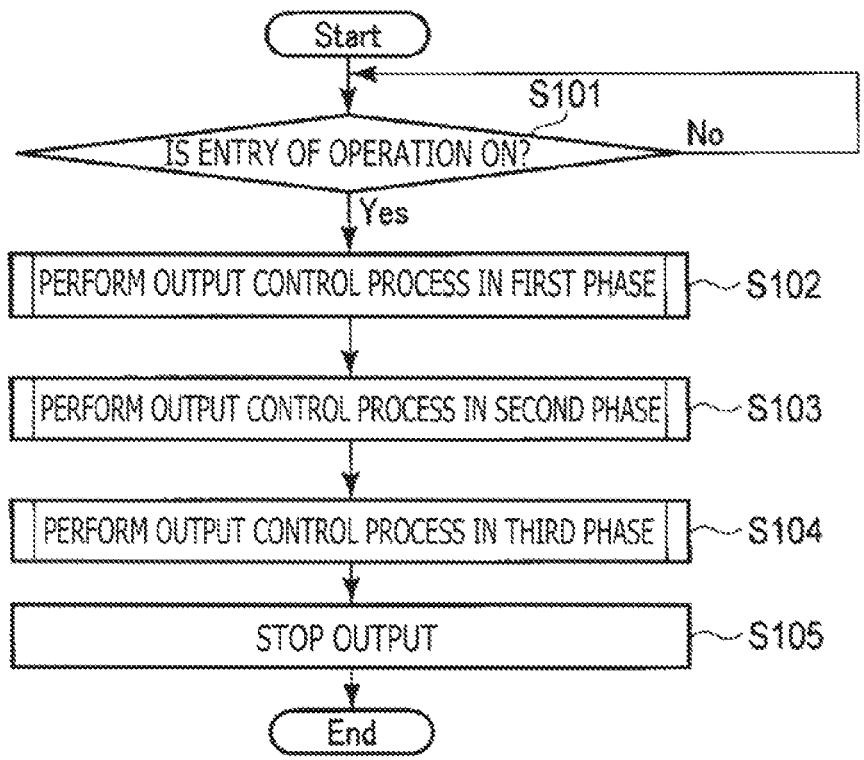
FIG. 3 is a flowchart of a processing sequence carried out by a processor of the energy source apparatus according to the first embodiment.

FIG. 3 is a flowchart of a processing sequence carried out by the processor 25 of the energy source apparatus 3. As illustrated in FIG. 3, the processor 25 determines whether or not an operation is entered through the operating member such as the foot switch 18 or the like, i.e., whether the entry of an operation is ON or OFF (S101). If an operation is not entered (S101-No), then processing returns to S101. In other words, the processor 25 waits until an operation is entered through the operating member. If an operation is entered (S101-Yes), then the processor 25 performs an output control process in a first phase on the output from the high-frequency power supply 31 and the output from the heater power supply 41 (S102). When the output control process in the first phase is finished, the processor 25 performs an output control process in a second phase on the output from the high-frequency power supply 31 and the output from the heater power supply 41 (S103). When the output control process in the second phase is finished, the processor 25 performs an output control process in a third phase on the output from the high-frequency power supply 31 and the output from the heater power supply 41 (S104). When the output control process in the third phase is finished, the processor 25 stops the output from the high-frequency power supply 31 and the output from the heater power supply 41 (S105).

Figure 4:
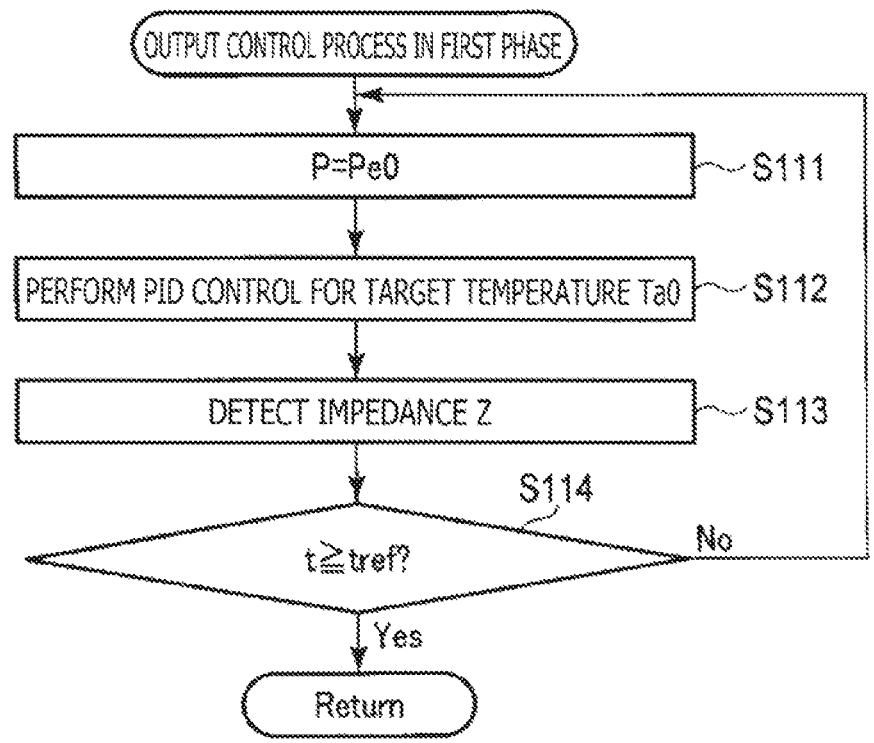
FIG. 4 is a flowchart of a processing sequence carried out by the processor according to the first embodiment in an output control process in a first phase.

FIG. 4 is a flowchart of a processing sequence carried out by the processor 25 in the output control process in the first phase (S102). In the first phase, the processor 25 starts to output the high-frequency electric power P from the high-frequency power supply 31 to the electrodes 21 and 22 and also starts to output the heater electric power P' from the heater power supply 41 to the heater 23. According to the present embodiment, when the high-frequency electric power P starts to be output, the processor 25 outputs the high-frequency electric power P from the high-frequency power supply 31 at a chronologically constant electric power value Pe (S111). At this time, the output current I and the output voltage V from the high-frequency power supply 31 are adjusted to keep the output electric power from the high-frequency power supply 31 as the constant electric power value Pe. According to the present embodiment, the electric power value Pe is a fixed value Pe0.

When the heater electric power P' starts to be output from the heater power supply 41, the processor 25 set a target temperature Ta, or a first target temperature, as a target value for the output from the heater power supply 41 to the heater 23, and performs a PID control process for the set target temperature Ta (S112). Specifically, an output control process is carried out on the output to the heater 23 for causing the temperature T of the heater 23 to reach the target temperature Ta and maintaining the temperature T of the heater 23 at the target temperature Ta. According to the PID control process for the target temperature Ta, the processor 25 detects the resistance R of the heater 23 based on the output current I' and the output voltage V' from the heater power supply 41 and detects the temperature T of the heater 23 based on the detected resistance R, as described hereinbefore. Then, the processor 25 adjusts the output electric power, i.e., the heater electric power P', the output current I', and the output voltage V' to the heater 23, based on the temperature deviation between the target temperature Ta and the temperature T of the heater 23, a time integral value of the temperature deviation, i.e., an integrated value of the temperature deviation, and a time differential value of the temperature deviation, i.e., a time rate of change of the temperature deviation, causing the temperature T to reach the target temperature Ta and maintaining the temperature T at the target temperature Ta. For example, if the temperature deviation between the target temperature Ta and the temperature T is large, then the processor 25 causes the heater power supply 41 to output the heater electric power P' at a large electric power value. If the temperature deviation between the target temperature Ta and the temperature T is small, and the temperature deviation is zero, then the processor 25 causes the heater power supply 41 to output the heater electric power P' at a small electric power value. According to the present embodiment, the target temperature Ta is of a fixed value Ta0 and is set in a range of 60° C. inclusive to approximately 100° C. According to an embodiment, the target temperature Ta is set in a range of 60° C. inclusive to 100° C. inclusive. According to another embodiment, the target temperature Ta is set in a range of 60° C. inclusive to 100° C. exclusive.

Then, the processor 25 detects the impedance Z based on the output current I and the output voltage V from the high-frequency power supply 31 (S113). In the first phase, the processor 25 detects an initial value Ze of the impedance Z as a value representing the impedance Z at the same time as or immediately after the start of the output from the high-frequency power supply 31, based on the detected impedance Z. The initial value Ze of the impedance Z is a parameter prior to the end of the second phase related to the impedance Z. The initial value Ze may represent the impedance Z at any point of time in the first phase, or may be an average value, a median value, or the like of the impedance Z in the first phase. The initial value Ze varies depending on a tissue volume of the treatment target including the thickness of a blood vessel. The initial value Ze varies depending on the state of the treatment target. Then, the processor 25 determines whether or not a time t from the start, used as a reference, of the output from the high-frequency power supply 31 is equal to or larger than a reference time tref (S114). In other words, it is determined whether or not the reference time tref has elapsed from the start of the first phase. If the time t is smaller than the reference time tref (S114-No), then processing goes back to step S111, and the steps from S111 are successively carried out. If the time t is equal to or larger than the reference time tref (S114-Yes), then the processor 25 puts an end to the output control process in the first phase, and starts the output control process in the second phase. The reference time tref is of a fixed value, for example, and is a short time of approximately 100 ms. Therefore, the time during which the output control process in the first phase is carried out is short and instantaneous. Consequently, the output control process in the first phase is finished before the impedance Z decreases from the initial value Ze to a minimum value Zmin to be described hereinafter.

Figure 5:
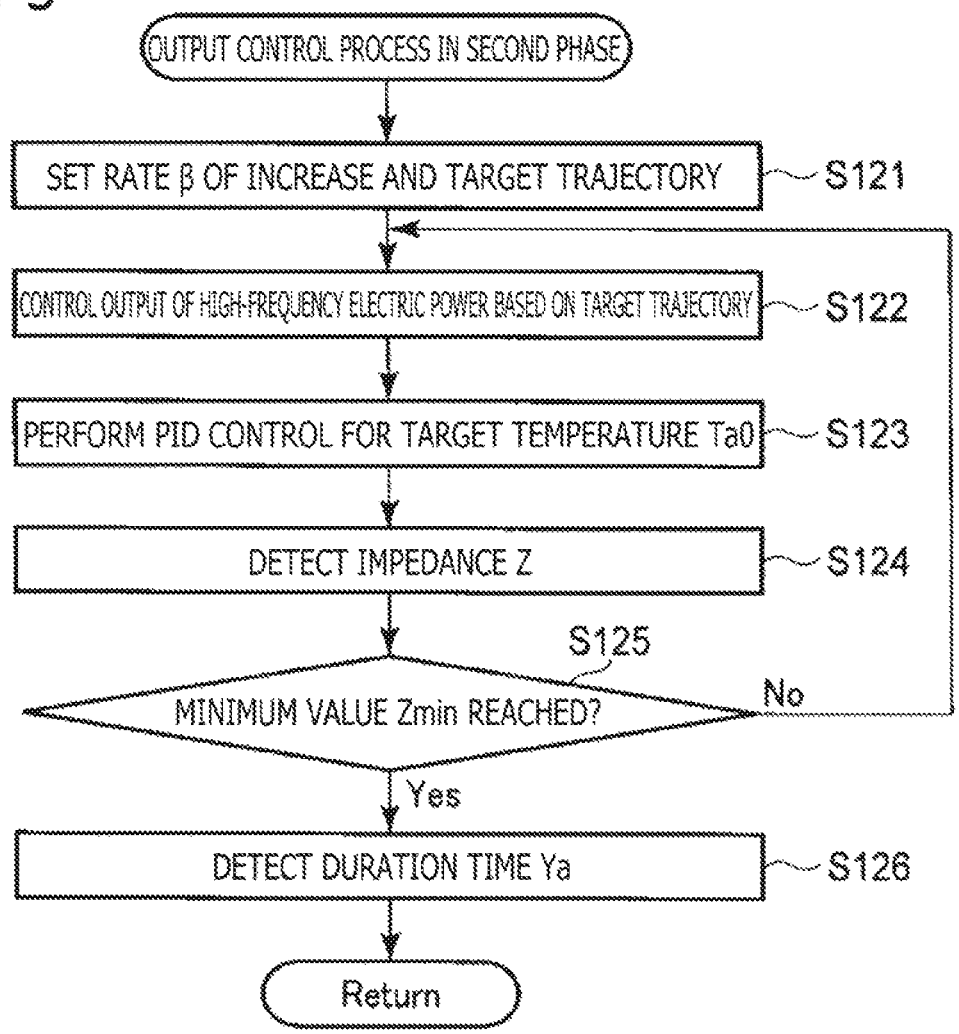
FIG. 5 is a flowchart of a processing sequence carried out by the processor according to the first embodiment in an output control process in a second phase.

FIG. 5 is a flowchart of a processing sequence carried out by the processor 25 in the output control process in the second phase (S103). In the second phase immediately after the first phase, the processor 25 sets a rate β of chronological increase of the output voltage V as a target value related to an output control process for controlling the output from the high-frequency power supply 31, based on the initial value Ze detected in the first phase (S121). At this time, the smaller the initial value Ze, the processor 25 sets the rate β of increase of the output voltage V to a larger value. Then, the processor 25 sets a target trajectory for the output voltage V in relation to the output control process on the output from the high-frequency power supply 31 in the second phase, based on the set rate β of increase (S121). According to the target trajectory, the output voltage V increases chronologically constantly at the set rate β of increase. Therefore, the smaller the initial value Ze, the processor 25 sets the gradient of the target trajectory to a larger value, and sets the value on the target trajectory to a larger value at each point of time in the second phase. Then, the processor 25 controls the output from the high-frequency power supply 31 to the electrodes 21 and 22 in a manner to have the output voltage V vary along the target trajectory (S122). In the second phase, the processor 25 also performs a PID control process for the target temperature Ta, or the first target temperature, on the output from the heater power supply 41 to the heater 23 (S123).

The processor 25 detects the impedance Z of the treatment target based on the output current I and the output voltage V from the high-frequency power supply 31 (S124). In the second phase, the treatment target is modified and the water in the treatment target starts to be boiled by the high-frequency current and the heater heat applied thereto. Until the water in the treatment target is boiled, the impedance Z decreases chronologically from the initial value Ze. When the water in the treatment target starts to be boiled, as the water in the treatment target starts to evaporate, the impedance Z starts to increase chronologically. Therefore, at the point of time when the water in the treatment target starts to be boiled or immediately close to that point of time, there occurs a minimum value Zmin of the impedance Z where the impedance Z switches from a chronologically decreasing state to a chronologically increasing state. In the second phase, the processor 25 determines whether or not the impedance Z has reached the minimum value Zmin based on the detected impedance Z (S125). According to an embodiment, the processor 25 detects the time when the impedance Z switches from the chronologically decreasing state to the chronologically increasing state in determining whether or not the impedance Z has reached the minimum value Zmin. Then, the processor 25 determines that the impedance Z has reached the minimum value Zmin at the time of switching based on the fact that the impedance Z has increased a reference value or more from the time of switching or that the impedance Z has been continuously larger than at the time of switching during a reference time or more from the time of switching.

If the processor 25 determines that the impedance Z has not reached the minimum value Zmin (S125-No), then processing goes back to step S122, and the steps from S122 are successively carried out. In the second phase, therefore, the processor 25 continues the output to the electrodes 21 and 22 and the output to the heater 23, continuously modifying the treatment target with the high-frequency current and the heater heat applied thereto, until the processor 25 detects that the impedance Z has reached the minimum value Zmin. If the processor 25 determines that the impedance Z has reached the minimum value Zmin (S125-Yes), then the processor 25 detects a time from the start of the second phase to the time when the processor 25 detects that the impedance Z has reached the minimum value Zmin, as a duration time Ya of the second phase (S126). When the processor 25 detects the duration time Ya of the second phase, the processor 25 puts an end to the output control process in the second phase, and starts the output control process in the third phase. Therefore, the time when the processor 25 detects the minimum value Zmin of the impedance Z is the time when the second phase is ended and the time when the third phase is started. The time when the minimum value Zmin is detected is subsequent to a point of time when the impedance Z has reached the minimum value Zmin, e.g., immediately after the point of time when the impedance Z has reached the minimum value Zmin.

The duration time Ya of the second phase is a parameter prior to the end of the second phase related to the impedance Z. The minimum value Zmin of the impedance Z, the time when the impedance Z reaches the minimum value Zmin, and the manner in which the impedance Z varies until it reaches the minimum value Zmin, etc. vary depending on the tissue volume of the treatment target including the thickness of a blood vessel, and vary depending on the state of the treatment target. Consequently, the duration time Ya of the second phase varies depending on the tissue volume of the treatment target and varies depending on the state of the treatment target. According to the present embodiment, the processor 25 detects the initial value Ze of the impedance Z and the duration time Ya of the second phase as parameters prior to the time when the processor 25 detects the minimum value Zmin related to the impedance Z, as described hereinbefore. According to the present embodiment, the processor 25 determines the tissue volume of the treatment target based on the initial value Ze and the duration time Ya that have been detected. At this time, according to an embodiment, the smaller the initial value Ze, the processor 25 determines that the tissue volume is larger. The longer the duration time Ya, the processor 25 determines that the tissue volume is larger.

FIG. 6 is a flowchart of a processing sequence carried out by the processor 25 in the output control process in the third phase (S104). In the third phase, the processor 25 sets a voltage value Va of the output voltage V as a target value with respect to the output control process for controlling the output from the high-frequency power supply 31, based on the initial value Ze and the duration time Ya that have been detected prior to the end of the second phase, i.e., based on the determined tissue volume of the treatment target (S131). At this time, the smaller the initial value Ze, the processor 25 sets the voltage value Va to a larger value, and the longer the duration time Ya, the processor 25 sets the voltage value Va to a larger value. Therefore, the larger the tissue volume, the larger the voltage value Va is set. Furthermore, the processor 25 sets a target temperature Tb for the heater 23 as a target value related to an output control process for controlling the output from the heater power supply 41, based on the initial value Ze and the duration time Ya that have been detected (S132). In setting the target temperature Tb, there is used a function, a table, or the like that represents the relationship of initial values Ze and duration times Ya to target temperatures Tb stored in the storage medium 26. At this time, the smaller the initial value Ze, the processor 25 sets the target temperature Tb to a higher value, and the longer the duration time Ya, the processor 25 sets the target temperature Tb to a higher value. Therefore, for example, the thicker a blood vessel as the treatment target, i.e., the larger the tissue volume, the higher the target temperature Tb is set. The target temperature Tb may be set to the target temperature Ta prior to the end of the second phase or higher, or may be set to a temperature lower than the target temperature Ta. At any rate, the target temperature Tb that is set is lower than a temperature of 200° C. or higher for incising the treatment target with the heater heat. If the processor 25 determines that the tissue volume of the treatment target is smaller than a reference value based on the initial value Ze and the duration time Ya, then the processor 25 sets the target temperature Tb to a temperature lower than the target temperature Ta prior to the end of the second phase.

Then, the processor 25 carries out a constant voltage control process for keeping the output voltage V chronologically constant at the set voltage value Va with respect to the output from the high-frequency power supply 31 (S133). The processor 25 carries out a PID control process for the target temperature Tb on the output from the heater power supply 41 (S134). In other words, the processor 25 performs the output control process for controlling the output to the heater 23 to cause the temperature T of the heater 23 to reach the target temperature Tb and keep the temperature T at the target temperature Tb. Then, the processor 25 detects the impedance Z of the treatment target based on the output current I and the output voltage V from the high-frequency power supply 31 (S135). In the third phase, the water in the treatment target is boiled continuously from the second phase by the high-frequency current and the heater heat applied thereto, and the water in the treatment target is evaporated continuously from the second phase. In the third phase, therefore, the impedance Z increases chronologically.

Then, the processor 25 determines whether or not the impedance Z is equal to or larger than a threshold value Zth (S136). According to the present embodiment, the threshold value Zth is a fixed value Zth0. If the impedance Z is smaller than the threshold value Zth (S136-No), then processing goes back to step S133, and the steps from S133 are successively carried out. In the third phase, therefore, the processor 25 continues the output to the electrodes 21 and 22 and the output to the heater 23, continuously modifying the treatment target with the high-frequency current and the heater heat applied thereto, until the impedance Z becomes equal to or larger than the threshold value Zth. If the impedance Z is equal to or larger than the threshold value Zth (S136-Yes), then the processor 23 puts an end to the output control process in the third phase. According to the present embodiment, the processor 25 stops the output to the electrodes 21 and 22 and the output to the heater 23 according to the processing of S105. According to the present embodiment, therefore, the threshold value Zth is used in determining whether to finish the third phase. When the impedance Z has increased to the threshold value Zth, the water in the treatment target is evaporated, causing the treatment target to be dehydrated. Consequently, when the impedance Z has increased to the threshold value Zth, the treatment target is dry and the boiling of the water in the treatment target has been finished.

Figure 8:
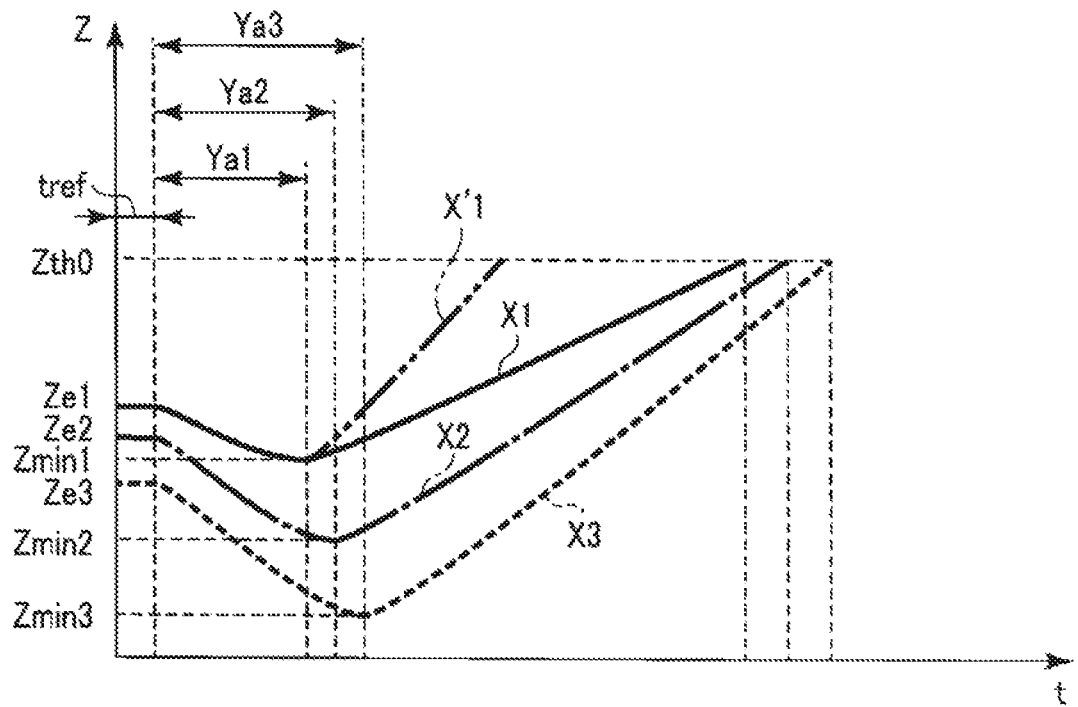
FIG. 8 is a schematic diagram illustrating an example of chronological changes in the impedance of a treatment target in case the target trajectories are set for the output voltage from the high-frequency power supply as illustrated in FIG. 7 according to the first embodiment.
Figure 9:
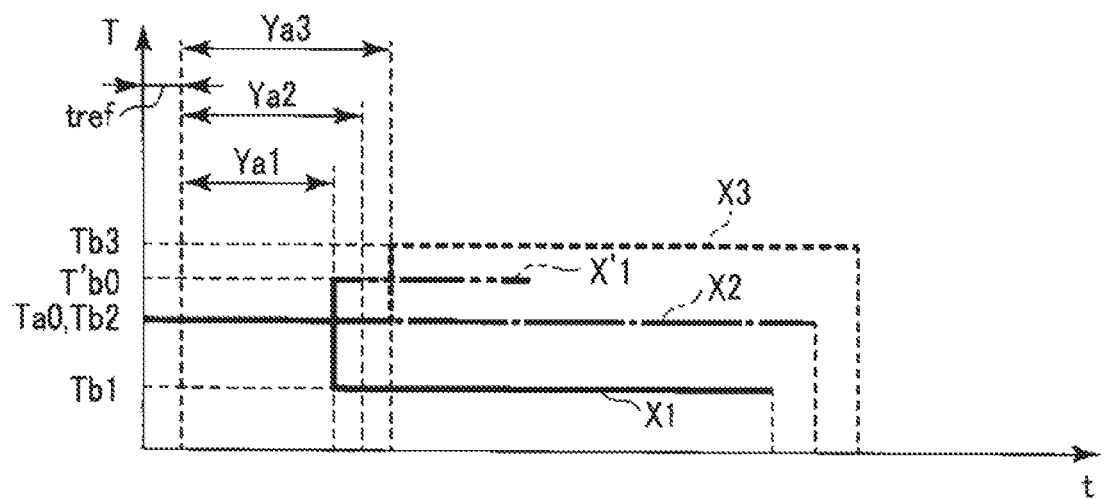
FIG. 9 is a schematic diagram illustrating an example of target trajectories for the temperature of a heater in case the target trajectories are set for the output voltage from the high-frequency power supply as illustrated in FIG. 7 according to the first embodiment.

FIG. 7 is a schematic diagram illustrating an example of target trajectories for the output voltage V from the high-frequency power supply 31 in the processing sequence carried out by the processor 25 as described hereinbefore. FIG. 8 is a schematic diagram illustrating an example of chronological changes in the impedance Z of the treatment target in case the target trajectories are set for the output voltage V from the high-frequency power supply 31 as illustrated in FIG. 7. FIG. 9 is a schematic diagram illustrating an example of target trajectories for the temperature T of the heater 23 in case the target trajectories are set for the output voltage V from the high-frequency power supply 31 as illustrated in FIG. 7. In each of FIGS. 7 through 9, a horizontal axis represents time t from the start, used as a reference, of the first phase. In FIG. 7, a vertical axis represents the output voltage V from the high-frequency power supply 31. In FIG. 8, a vertical axis represents the impedance Z. In FIG. 9, a vertical axis represents the temperature T of the heater 23. Each of FIGS. 7 through 9 illustrates the chronological changes in three states X1 through X3, or tissue states. The states X1 through X3 indicate tissue volumes of the treatment target that are different from each other. In the state X1, the tissue volume of the treatment target is smaller because the blood vessel as the treatment target is thin, etc. than in the state X2. In the state X3, the tissue volume of the treatment target is larger because the blood vessel as the treatment target is thick, etc. than in the state X2. In each of FIGS. 7 through 9, the chronological changes in the state X1 are indicated by the solid-line curve, the chronological changes in the state X2 by the dot-and-dash-line curve, and the chronological changes in the state X3 by the broken-line curve. In FIGS. 8 and 9, the chronological changes in the impedance Z in a state X'1 are indicated by the two-dot-and-dash-line curve as a comparative example. The tissue volume in the state X'1 is substantially the same as the tissue volume in the state X1. However, the output to the heater 23 in the three phase in the state X'1 is different from that in the state X1.

The larger the tissue volume of the treatment target, the smaller the initial value Ze of the impedance Z detected in the first phase. In the examples illustrated in FIGS. 7 through 9, actually, the initial value Ze1 in the state X1 is larger than the initial value Ze2 in the state X2, and the initial value Ze3 in the state X3 is smaller than the initial value Ze2 in the state X2. According to the present embodiment, as described hereinbefore, the smaller the initial value Ze of the impedance Z, the rate β of increase of the output voltage V in the second phase is set to a larger value and the gradient of the target trajectory for the output voltage V in the second phase is set to a larger value. In the state X1, actually, the rate β of increase of the output voltage V and the gradient of the target trajectory in the second phase are set to smaller values than in the state X2. In the state X3, the rate β of increase of the output voltage V and the gradient of the target trajectory in the second phase are set to larger values than in the state X2.

The larger the tissue volume of the treatment target, the smaller the minimum value Zmin of the impedance Z. The larger the tissue volume of the treatment target, the longer the time required until the impedance Z reaches the minimum value Zmin. Therefore, the larger the tissue volume of the treatment target, the longer the duration time Ya in the second phase. Actually, a minimum value Zmin1 in the state X1 is larger than a minimum value Zmin2 in the state X2. The time required until the impedance Z reaches the minimum value Zmin1 in the state X1 is shorter than the time required until the impedance Z reaches the minimum value Zmin2 in the state X2. Therefore, a duration time Ya1 in the second phase in the state X1 is shorter than a duration time Ya2 in the second phase in the state X2. Moreover, a minimum value Zmin3 in the state X3 is smaller than the minimum value Zmin2 in the state X2. The time required until the impedance Z reaches the minimum value Zmin3 in the state X3 is longer than the time required until the impedance Z reaches the minimum value Zmin2 in the state X2. Therefore, a duration time Ya3 in the second phase in the state X3 is longer than the duration time Ya2 in the second phase in the state X2.

According to the present embodiment, as described hereinbefore, the smaller the initial value Ze of the impedance and the longer the duration time Ya of the second phase, it is determined that the tissue volume of the treatment target is larger. Therefore, the voltage value Va of the output voltage V in the constant voltage control process in the third phase is set to a larger value. Actually, the voltage value Va1 in the third phase set in the state X1 is smaller than the voltage value Va2 in the third phase set in the state X2. The voltage value Va3 in the third phase set in the state X3 is larger than the voltage value Va2 in the third phase set in the state X2.

According to the present embodiment, as described hereinbefore, the smaller the initial value Ze of the impedance and the longer the duration time Ya of the second phase, it is determined that the tissue volume of the treatment target is larger. Therefore, the target temperature Tb in the PID control process in the third phase is set to a higher value. Actually, the target temperature Tb1 in the third phase set in the state X1 is lower than the target temperature Tb2 in the third phase set in the state X2. The target temperature Tb3 in the third phase set in the state X3 is higher than the target temperature Tb2 in the third phase set in the state X2. According to an embodiment, the target temperature Tb set in the state X2 is substantially the same as the target temperature Ta0 prior to the end of the second phase, and the target temperature Tb set in the state X3 is higher than the target temperature Ta0 prior to the end of the second phase. Furthermore, in the state X1, the processor 25 determines that the tissue volume of the treatment target is smaller than the reference value based on the initial value Ze and the duration time Ya. Therefore, in the state X1, the processor 25 sets the target temperature Tb1, or a second target temperature, to a lower value than the target temperature Ta0, or the first target temperature, prior to the time when the minimum value Zmin is detected. In the state X1, therefore, the output control process is performed on the output from the heater power supply 41 in the third phase to lower the heater 23 from the target temperature Ta0 to the target temperature Tb1 and keep the heater 23 at the target temperature Tb1.

Here, the comparative example in which the target temperature Tb in the third phase is set to a fixed value T'b0 and the PID control process is carried out on the output to the heater 23 regardless of the initial value Ze of the impedance Z and the duration time Ya of the second phase, i.e., regardless of the tissue volume, will be described hereinafter. The fixed value T'b0 of the target temperature Tb in the comparative example is higher than the target temperature Ta0 prior to the time when the minimum value Zmin is detected. According to the comparative example, the output control process for controlling the output from the heater power supply 41 is carried out in the third phase for the target temperature T'b0 even in the state X'1 where the tissue volume is small as with the state X1. In the state X'1, therefore, the amount of heater heat applied to the treatment target in the third phase is larger than in the state X1. Since the large amount of heat is applied to the treatment target whose tissue volume is small, the amount of water evaporated per unit volume of the treatment target subsequent to the start of the third phase increases rapidly in the state X'1. In the state X'1, therefore, subsequent to the time when the minimum value Zmin is detected, the impedance Z increases rapidly, and the treatment target is quickly dehydrated and dried.

According to the present embodiment, on the other hand, if the tissue volume of the treatment target in the state X1 or the like is small, the target temperature Tb in the third phase is set to a lower value than the target temperature Ta0 prior to the time when the minimum value Zmin is detected. In the third phase, the output control process for controlling the output from the heater power supply 41 is performed for the lower target temperature Tb. Consequently, if the tissue volume of the treatment target in the state X1 or the like is small, the amount of heater heat applied to the treatment target is small. Therefore, even if the tissue volume of the treatment target is small, the amount of water evaporated per unit volume of the treatment target by the heater heat subsequent to the start of the third phase is prevented from increasing rapidly. In case the tissue volume of the treatment target is small, therefore, the impedance Z rises gradually subsequent to the time when the minimum value Zmin is detected, and the time required until the treatment target is dehydrated, i.e., the time required until the treatment target is dried, is long. As the time required until the treatment target is dehydrated is long, the time during which the water in the treatment target is boiled becomes long.

The longer the time in which the water in the treatment target is boiled, the longer the time in which the treatment target is welded, i.e., the time in which the treatment target is fused, increasing the ability to seal and coagulate the treatment target. According to the present embodiment, since the output control process for controlling the output from the heater power supply 41 is carried out in the third phase, even if the tissue volume of the treatment target is small, the time in which the water in the treatment target is boiled is long. Consequently, in case the tissue volume of the treatment target is small, the time in which the treatment target is welded and fused is long, causing the treatment target to be appropriately welded and fused, and causing the treatment target to be appropriately sealed and coagulated.

According to the present embodiment, as described hereinbefore, the state of the treatment target such as the tissue volume of the treatment target, etc. is appropriately detected based on the initial value Ze of the impedance Z and the duration time Ya of the second phase. Based on the detected state of the treatment target, the output from the heater power supply 41 in the third phase is appropriately controlled. Specifically, the output control process for controlling the output to the heater 23 in the third phase is performed in a manner to increase the time in which the water in the treatment target is boiled and to increase the time in which the treatment target is welded depending on the state of the treatment target. Therefore, the treatment target is appropriated sealed and coagulated regardless of the state of the treatment target such as the tissue volume of the treatment target, etc.

According to the present embodiment, furthermore, prior to the time when the minimum value Zmin is detected, the output from the heater power supply 41 is started, and the output control process for controlling the output to the heater 23 is continuously performed for the target temperature Ta in the second phase. At the target temperature Ta, the treatment target is modified by the heater heat. As the treatment target is continuously modified by the heater heat in the second phase prior to the time when the minimum value Zmin is detected, the treatment target quickly changes to the state described hereinbefore in which the water in the treatment target is boiled after the output to the electrodes 21 and 22 is started in the first phase. Since the time from the start of the output from the high-frequency power supply 31 until the state in which the water in the treatment target is boiled is shortened, the ability to seal and coagulate the treatment target is increased, and the energy efficiency for the treatment is increased.

Modifications of the First Embodiment

According to the first embodiment, the processor 25 sets the target temperature Tb as a target value for the output control process for controlling the output to the heater 23 based on the initial value Ze of the impedance Z and the duration time Ya of the second phase. However, the disclosed technology is not limited to such details. According to a modification, the processor 25 determines the tissue volume of the treatment target based on the minimum value Zmin of the impedance Z, the time when the impedance Z reaches the minimum value Zmin, and a rate of reduction of the impedance Z to the minimum value Zmin, etc. instead of the initial value Ze and the duration time Ya or in addition to the initial value Ze and the duration time Ya, and sets the target temperature Tb for the heater 23 in the third phase. The minimum value Zmin of the impedance Z, the time when the impedance Z reaches the minimum value Zmin, and the rate of reduction of the impedance Z to the minimum value Zmin are parameters prior to the end of the second phase related to the impedance Z. For example, if the target temperature Tb is to be set based on the minimum value Zmin, then the smaller the minimum value Zmin, the processor 25 determines that the tissue volume of the treatment target is larger, and sets the target temperature Tb in the third phase to a higher value.

According to a modification, the processor 25 sets the target temperature Tb for the heater 23 in the third phase based on either one of the output electric power, i.e., the high-frequency electric power P, the output current I, and the output voltage V from the high-frequency power supply 31 prior to the time when the minimum value Zmin is detected. In other words, the target temperature Tb is set based on a parameter prior to the end of the second phase related to the output from the high-frequency power supply 31. For example, if the output control process for controlling the output from the high-frequency power supply 31 is performed in the second phase in the same manner as with the first embodiment, then the larger the tissue volume of the treatment target, the larger the high-frequency electric power P that is output in the second phase. According to the present modification, therefore, the larger the high-frequency electric power P that is output in the second phase, for example, the processor 25 determines that the tissue volume of the treatment target is larger, and sets the target temperature Tb in the third phase to a higher value.

According to the embodiment described hereinbefore, etc., the output to the heater 23 takes place in the first phase. According to a modification, the heater electric power P' to the heater 23 is started at the start of the second phase. In this case, the processor 25 maintains the stoppage of the output to the heater 23 in the first phase, instead of performing the processing of S112. According to the present modification, the output to the heater 23 is controlled for the target temperature Ta according to the processing of S123 in the second phase. Therefore, in the second phase, the treatment target is continuously modified by the heater heat, and the treatment target changes to the state described hereinbefore in which the water therein is boiled.

According to a modification, furthermore, the rate β of increase of the output voltage V that is a target value related to the output control process for controlling the output from the high-frequency power supply 31 in the second phase is of a fixed value β0 regardless of the initial value Ze, i.e., regardless of the tissue volume of the treatment target. In this case, the processor 25 does not perform the processing of S121 for setting the rate β of increase and the target trajectory based on the initial value Ze. According to a modification, moreover, the voltage value Va that is a target value related to the output control process for controlling the output from the high-frequency power supply 31 in the third phase is of a fixed value Va0 regardless of the parameters described hereinbefore, i.e., Ze, Ya, Zmin, etc. such as the initial value Ze, the duration time Ya, etc., i.e., regardless of the tissue volume of the treatment target. In this case, the processor 25 does not perform the processing of S131 for setting the voltage value Va based on the parameters, i.e., Ze, Ya, Zmin, etc.

According to a modification, furthermore, either one of a constant power control process for keeping the output electric power from the high-frequency power supply 31, i.e., the high-frequency electric power P, at a constant electric power value Pa, and a constant current control process for keeping the output current I therefrom at a constant current value Ia is carried out in the third phase. For performing the constant power control process, the processor 25 may set the electric power value Pa that is a target value to a fixed value Pa0 regardless of the detected parameters, i.e., Ze, Ya, etc., or may set the electric power value Pa based on the detected parameters, i.e., Ze, Ya, etc. If the processor 25 is to set the electric power value Pa based on the parameters, i.e., Ze, Ya, etc., then the longer the duration time Ya, i.e., the larger the tissue volume of the treatment target, for example, the processor 25 sets the electric power value Pa to a larger value. Similarly, for performing the constant current control process, the processor 25 may set the current value Ia that is a target value to a fixed value Ta0 regardless of the detected parameters, i.e., Ze, Ya, etc., or may set the current value Ia based on the detected parameters, i.e., Ze, Ya, etc. If the processor 25 is to set the current value Ia based on the parameters, i.e., Ze, Ya, etc., then the longer the duration time Ya, i.e., the larger the tissue volume of the treatment target, for example, the processor 25 sets the current value Ia to a larger value.

According to a modification, moreover, the processor 25 switches between the constant voltage control process, the constant power control process, and the constant current control process based on the impedance Z in the third phase. In this case, the processor 25 switches between the constant voltage control process, the constant power control process, and the constant current control process based on a switching valve Zs1 and a switching value Zs2 larger than the switching value Zs1. For example, if the impedance Z is smaller than the switching value Zs1, then the processor 25 carries out the constant current control process described hereinbefore on the output from the high-frequency power supply 31. If the impedance Z is equal to or larger than the switching value Zs1 and smaller than the switching value Zs2, then the processor 25 carries out the constant power control process described hereinbefore on the output from the high-frequency power supply 31. If the impedance Z is equal to or larger than the switching value Zs2, then the processor 25 carries out the constant voltage control process described hereinbefore on the output from the high-frequency power supply 31. According to the present modification, the threshold Zth for the impedance Z that is used in determining whether to finish the third phase is set to a value larger than the switching values Zs1 and Zs2.

According to a modification, furthermore, the processor 25 sets a target trajectory for the impedance Z in the third phase, and controls the output from the high-frequency power supply 31 in a manner to have the impedance Z vary along the set target trajectory. In this case, the high-frequency electric power P, the output current I, and the output voltage V from the high-frequency power supply 31 are adjusted in a manner to have the impedance Z vary along the set target trajectory. A target trajectory for the impedance Z may be set to a predetermined trajectory regardless of the detected parameters, i.e., Ze, Ya, etc. or may be set based on the detected parameters, i.e., Ze, Ya, etc. According to a modification, moreover, the processor 25 stops the output from the high-frequency power supply 31 in the third phase, instead of performing the processing of S133. In this case, in the third phase, the treatment target is continuously modified and the water in the treatment target is continuously boiled by the heater heat.

According to the embodiment described hereinbefore, etc., if the processor 25 determines that the tissue volume of the treatment target is smaller than the reference value based on the detected parameters, i.e., Ze, Ya, etc., then the processor 25 sets the target temperature Tb in the third phase to a value lower than the target temperature Ta prior to the time when the minimum value Zmin is detected. However, the disclosed technology is not limited to such details. According to a modification, if the processor 25 determines that the tissue volume of the treatment target is smaller than the reference value based on the detected parameters, i.e., Ze, Ya, etc., then the processor 25 continuously stops the output from the high-frequency power supply 31 in the third phase. In this case, the processor 25 determines whether or not the output to the heater 23 is required in the third phase based on the parameters, i.e., Ze, Ya, etc., in addition to the processing of S132 for setting the target temperature Tb in the third phase based on the parameters, i.e., Ze, Ya, etc. According to the present modification, therefore, if the tissue volume of the treatment target in the state X1 or the like is small, the heater electric power P' to the heater 23 is not output and the heater 23 does not produce heat in the third phase. Even in this case, in the third phase, the treatment target is continuously modified and the water in the treatment target is continuously boiled by the heat caused by the high-frequency current and the heater heat produced prior to the third phase. According to the present modification, if the tissue volume of the treatment target in the states X2, X3, or the like is equal to or larger than the reference value, then the output to the heater 23 is continued, causing the heater 23 to produce heat in the third phase. If the processor 25 determines that the tissue volume of the treatment target is equal to or larger than the reference value, then the longer the duration time Ya, i.e., the larger the tissue volume of the treatment target, for example, the processor 25 sets the target temperature Tb in the third phase to a higher value.

According to the embodiment described hereinbefore, the threshold value Zth that is used in determining whether to finish the third phase is of the fixed value Zth0. However, the disclosed technology is not limited to such details. According to a modification, the processor 25 sets the threshold value Zth for the impedance Z as a target value related to the output control process for controlling the output to the heater 23 in the third phase, based on the parameters described hereinbefore, i.e., Ze, Ya, etc. In this case, the longer the duration time Ya in the second phase, i.e., the larger the tissue volume of the treatment target, for example, the processor 25 sets the threshold value Zth as a target value to a higher value.

According to a modification, furthermore, a threshold value Ybth for an elapsed time Yb from the start of the third phase is set as a target value related to the output control process for controlling the output to the heater 23 in the third phase, rather than the threshold value Zth for the impedance Z. In this case, the threshold value Ybth for the elapsed time Yb is used in determining whether to finish the third phase. The threshold value Ybth for the elapsed time Yb may be a fixed value Ybth0 or may be set based on the parameters described hereinbefore, i.e., Ze, Ya, etc. If the threshold value Ybth is to be set based on the parameters described hereinbefore, i.e., Ze, Ya, etc., then the longer the duration time Ya in the second phase, i.e., the larger the tissue volume of the treatment target, for example, the processor 25 sets the threshold value Ybth as a target value to a longer value.

Second Embodiment

A second embodiment of the disclosed technology will be described hereinafter with reference to FIGS. 10 through 12. According to the second embodiment, the processing according to the first embodiment is modified as described hereinafter. Those parts of the second embodiment which are identical to those of the first embodiment are denoted by identical numeral references, and will not be described hereinafter.

Figure 10:
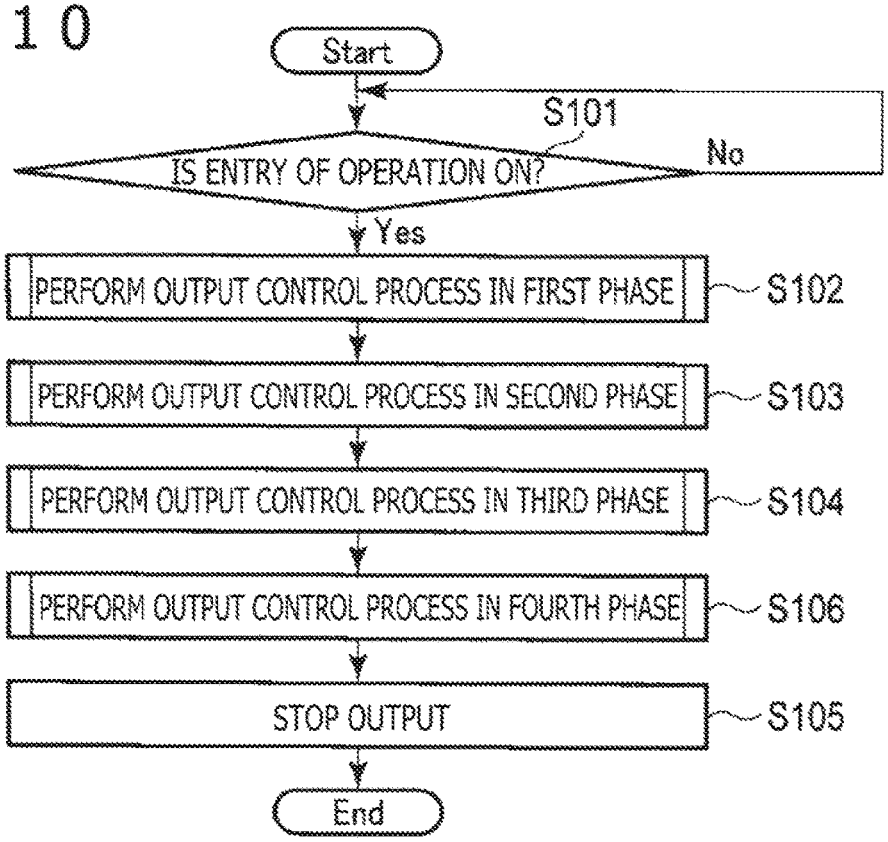
FIG. 10 is a flowchart of a processing sequence carried out by a processor of an energy source apparatus according to a second embodiment.

FIG. 10 is a flowchart of a processing sequence carried out by a processor 25 of an energy source apparatus 3 according to the present embodiment. According to the present embodiment, as illustrated in FIG. 10, as with the embodiment described hereinbefore, etc., if an operation is entered through the operating member (S101-Yes), then the processor 25 successively performs the output control process in the first phase (S102), the output control process in the second phase (S103), and the output control process in the third phase (S104) on the output from the high-frequency power supply 31 and the output from the heater power supply 41. According to the present embodiment, however, when the output control process in the third phase is finished, the processor 25 performs an output control process in a fourth phase (S106) on the output from the high-frequency power supply 31 and the output from the heater power supply 41. When the output control process in the fourth phase is finished, the processor 25 stops the output from the high-frequency power supply 31 and the output from the heater power supply 41 (S105). In a treatment according to the present embodiment, after the treatment target is sealed or coagulated by the high-frequency current and the heater heat, as described hereinbefore, the treatment target is incised by the heater heat applied thereto.

Figure 11:
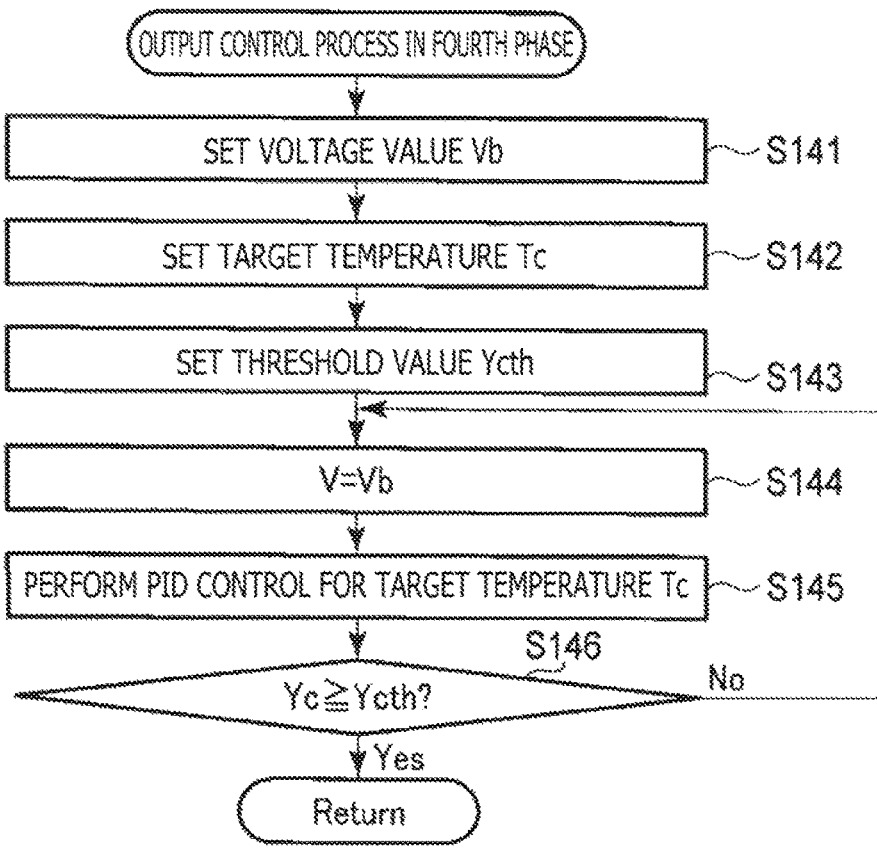
FIG. 11 is a flowchart of a processing sequence carried out by the processor according to the second embodiment in an output control process in a fourth phase.

FIG. 11 is a flowchart of a processing sequence carried out by the processor 25 in the output control process in the fourth phase (S106). In the fourth phase, the processor 25 sets a voltage value Vb for the output voltage V as a target value related to the output control process for controlling the output from the high-frequency power supply 31, based on the parameters, i.e., Ze, Ya, Zmin, etc. detected prior to the end of the second phase, such as the initial value Ze, the duration time Ya, etc., i.e., based on the determined tissue volume of the treatment target (S141). At this time, the smaller the initial value Ze, the processor 25 sets the voltage value Vb to a larger value, and the longer the duration time Ya, the processor 25 sets the voltage value Vb to a larger value. Consequently, the larger the tissue volume, the voltage value Vb is set to a larger value. Then, the processor 25 sets a target temperature Tc for the heater 23 as a target value related to the output control process for controlling the output from the heater power supply 41, based on the detected parameters, i.e., Ze, Ya, Zmin, etc. (S142). At this time, the smaller the initial value Ze, the processor 25 sets the target temperature Tc to a higher value, and the longer the duration time Ya, the processor 25 sets the target temperature Tc to a higher value. Consequently, the thicker a blood vessel as the treatment target, i.e., the larger the tissue volume, the target temperature Tc is set to a higher value. At any rate, the target temperature Tc is a temperature at which the treatment target can be incised, and is higher than the target temperature Ta in the second phase. The target temperature Tc in the fourth phase is higher than the target temperature Tb set in the third phase. According to an embodiment, the target temperature Tc is set in a range equal to or higher than 200° C., for example.

Then, the processor 25 sets a threshold value Ycth used in determining whether to finish the fourth phase with respect to the elapsed time Yc from the start of the fourth phase, based on the detected parameters, i.e., Ze, Ya, Zmin, etc. (S143). At this time, the smaller the initial value Ze, the processor 25 sets the threshold value Ycth to a longer value, and the longer the duration time Ya, the processor 25 sets the threshold value Ycth to a longer value. Therefore, the larger the tissue volume, the threshold value Ycth for the elapsed time Yc is set to a longer value.

Then, the processor 25 carries out a constant voltage control process for keeping the output voltage V chronologically constant at the set voltage value Vb with respect to the output from the high-frequency power supply 31 (S144). Then, the processor 25 carries out a PID control process for the target temperature Tc on the output from the heater power supply 41 (S145). In other words, the processor 25 performs the output control process for controlling the output to the heater 23 to cause the temperature T of the heater 23 to rise to the target temperature Tc and keep the temperature T at the target temperature Tc. As described hereinbefore, the target temperature Tc in the fourth phase is higher than the target temperature Tb in the third phase. Therefore, the processor 25 increases the output to the heater 23 by switching from the third phase to the fourth phase. When the third phase switches to the fourth phase, the output voltage V', the output electric power, i.e., the heater electric power P', etc. from the heater power supply 41 increase. At the start of the fourth phase, the impedance Z has risen to the threshold value Zth described hereinbefore, and the treatment target has been dried, ending the state in which the water in the treatment target is boiled. Therefore, the treatment target is incised using the heater heat while the treatment target is dry after it has been sealed or coagulated.

Then, the processor 25 determines whether or not the elapsed time Yc from the start of the fourth phase is equal to or larger than the threshold value Ycth (S146). If the elapsed time Yc is shorter than the threshold value Ycth (S146-No), then processing goes back to step S144, and the steps from S144 are successively carried out. In the fourth phase, therefore, the processor 25 continues the output to the electrodes 21 and 22 and the output to the heater 23 until the elapsed time Yc becomes equal to or larger than the threshold value Ycth. If the elapsed time Yc is equal to or larger than the threshold value Ycth (S146-Yes), then the processor 25 puts an end to the output control process in the fourth phase. According to the present embodiment, the processor 25 stops the output to the electrodes 21 and 22 and the output to the heater 23 according to the processing of S105.

Figure 12:
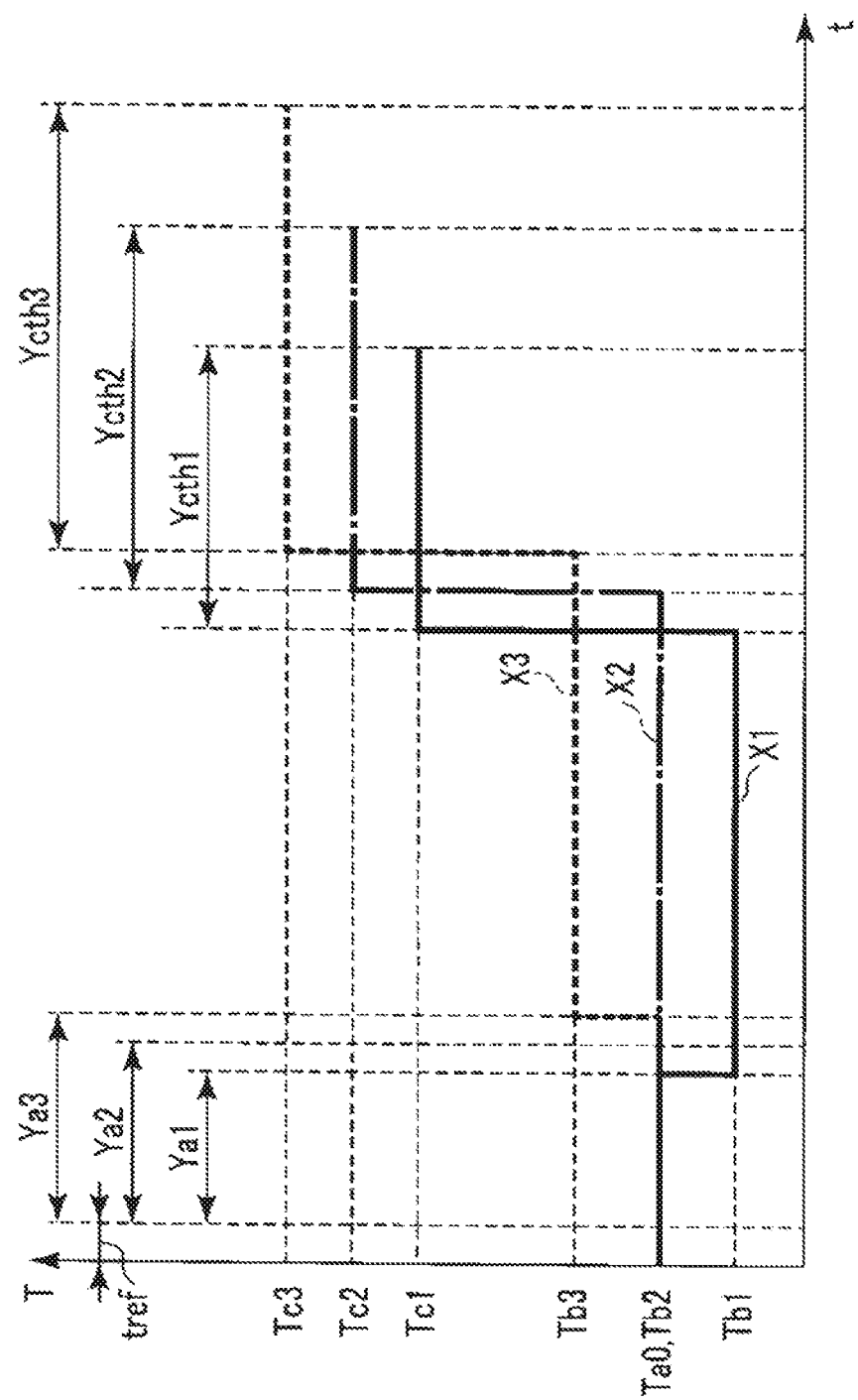
FIG. 12 is a schematic diagram illustrating an example of target trajectories for the temperature of the heater in the processing sequence carried out by the processor according to the second embodiment.

FIG. 12 is a schematic diagram illustrating an example of target trajectories for the temperature T of the heater 23 in the processing sequence described hereinbefore carried out by the processor 25. In FIG. 12, a horizontal axis represents time t from the start, used as a reference, of the first phase, and a vertical axis represents the temperature T of the heater 23. FIG. 12 illustrates the target trajectories in the three states X1 through X3, or tissue states. In FIG. 12, the chronological changes in the state X1 are indicated by the solid-line curve, the chronological changes in the state X2 by the dot-and-dash-line curve, and the chronological changes in the state X3 by the broken-line curve.

As illustrated in FIG. 12, according to the present embodiment, the target temperature Tc in the PID control process in the fourth phase is set to a value higher than the target temperature Ta0 in the second phase in any one of the states X1 through X3. For example, the target temperature Tc is 200° C. or higher in any one of the states X1 through X3. Consequently, in any one of the states X1 through X3, the treatment target is incised by the heater heat in the fourth phase. In any one of the states X1 through X3, the target temperature Tc in the fourth phase is set to a value higher than the target temperature Tb in the third phase. Consequently, in any one of the states X1 through X3, the output to the heater 23 rises by switching from the third phase to the fourth phase.

According to the present embodiment, as described hereinbefore, the smaller the initial value Ze of the impedance Z and the longer the duration time Ya of the second phase, it is determined that the tissue volume of the treatment target is larger. Therefore, the target temperature Tc in the PID control process in the fourth phase is set to a higher value. Actually, a target temperature Tc1 in the fourth phase set in the state X1 is lower than a target temperature Tc2 in the fourth phase set in the state X2. A target temperature Tc3 in the fourth phase set in the state X3 is higher than the target temperature Tc2 in the fourth phase set in the state X2. According to the present embodiment, since the smaller the initial value Ze of the impedance Z and the longer the duration time Ya of the second phase, it is determined that the tissue volume of the treatment target is larger, as described hereinbefore, the threshold value Ycth for the elapsed time Yc that is used in determining whether to finish the fourth phase is set to a longer value. Actually, a threshold value Ycth1 set in the state X1 is shorter than a threshold value Ycth2 set in the state X2. A threshold value Ycth3 set in the state X3 is longer than the threshold value Ycth2 set in the state X2.

According to the present embodiment, as with the embodiment described hereinbefore, etc., the state of the treatment target is appropriately detected based on the parameters prior to the end of the second phase, such as the initial value Ze of the impedance Z, the duration time Ya of the second phase, etc. Then, based on the detected state of the treatment target, the output from the heater power supply 41 in the third phase is appropriately controlled. Specifically, the output control process for controlling the output to the heater 23 in the third phase is carried out in a manner to increase the time during which the water in the treatment target is boiled and to increase the time during which the treatment target is welded, depending on the state of the treatment target. Therefore, the treatment target is appropriately sealed and coagulated regardless of the state of the treatment target such as the tissue volume of the treatment target, etc. Furthermore, according to the present embodiment, the treatment target that has been appropriately sealed and coagulated in the third phase is appropriately incised in the fourth phase.

Modifications of the Second Embodiment

The output control process for controlling the output from the high-frequency power supply 31 in the fourth phase is not limited to the control process according to the second embodiment. According to a modification, the voltage value Vb that is a target value related to the output control process for controlling the output from the high-frequency power supply 31 is a fixed value Vb0 regardless of the tissue volume of the treatment target. According to a modification, either one of the constant power control process for keeping the output electric power from the high-frequency power supply 31, i.e., the high-frequency electric power P, at a constant electric power value Pb, and the constant current control process for keeping the output current I therefrom at a constant current value Ib is carried out in the fourth phase. At this time, the processor 25 may set each of the electric power value Pb and the current value Ib to a fixed value regardless of the detected parameters, i.e., Ze, Ya, etc. or may set them based on the detected parameters, i.e., Ze, Ya, etc. According to a modification, the processor 25 switches between the constant voltage control process, the constant power control process, and the constant current control process based on the impedance Z in the fourth phase.

According to a modification, the processor 25 sets a target trajectory for the impedance Z in the fourth phase, and controls the output from the high-frequency power supply 31 in a manner to have the impedance Z vary along the set target trajectory. In this case, a target trajectory is set in a manner to have the impedance increase chronologically constantly from the threshold value Zth at the end of the third phase. Moreover, a target trajectory for the impedance may be set to a predetermined trajectory regardless of the detected parameters, i.e., Ze, Ya, etc. or may be set based on the detected parameters, i.e., Ze, Ya, etc. According to a modification, furthermore, the processor 25 stops the output from the high-frequency power supply 31 in the fourth phase, instead of performing the processing of S144. In this case, in the fourth phase, only the heater heat is applied to the treatment target.

According to a modification, the target temperature Tc in the fourth phase is set to a fixed value Tc0 regardless of the detected parameters, i.e., Ze, Ya, etc. In this case, the target temperature Tc0 is a temperature of 200° C. or higher, for example, for incising the treatment target, and is higher than the target temperature Ta in the second phase. The target temperature Tc0 in the fourth phase is higher than the target temperature Tb set in the third phase.

According to a modification, the threshold value Ycth for the elapsed time Yc that is used in determining whether to finish the fourth phase may be a fixed value Ycth0. According to a modification, a threshold value Zath for the impedance Z that is different from the threshold value Zth is used in determining whether to finish the fourth phase, instead of the threshold value Ycth for the elapsed time Yc. In this case, the threshold value Zath is higher than the threshold value Zth that is used in determining whether to finish the third phase. The threshold value Zath for the impedance Z may be a fixed value regardless of the detected parameters, i.e., Ze, Ya, etc. or may be set based on the detected parameters, i.e., Ze, Ya, etc. In the fourth phase, as the temperature of the treatment target rises due to the heater heat, etc., the impedance Z increases chronologically from the threshold value Zth that is used in determining whether to finish the third phase.

According to the embodiment, etc. hereinabove, when the third phase or the forth phase is ended or immediately after the end of the sealing phase, the output from the high-frequency power supply 31 and the output from the heater power supply 41 are stopped by the processing of S105. However, the disclosed technology is not limited to such details. According to a modification, the processor 25 causes the output to the heater 23 to be continued instead of carrying out the processing of S105. In this case, the output from the heater power supply 41 is controlled to be lowered to prevent the treatment target from being modified by the heater heat. In the modification, the processor 25 causes the heater power supply 41 to stop the output upon elapse of a certain time from the end of the third phase or the end of the fourth phase, or based on an operation made by the surgeon or the like.

Furthermore, according to a modification, the processor 25 continues the output to the electrodes 21 and 22, instead of performing the processing of S105. In this case, however, the output from the high-frequency power supply 31 is controlled to reduce the output from the high-frequency power supply 31 in a manner not to modify the treatment target with the high-frequency current. According to the present modification, the processor 25 stops the output from the high-frequency power supply 31 upon elapse of a certain time from the end of the third phase or the end of the fourth phase or based on an operation entered by the surgeon or the like.

In the embodiment described hereinbefore, etc., the energy output source (31, 41) of the energy source apparatus (3) outputs high-frequency electric power (P) to the bipolar electrodes (21, 22) thereby to cause a high-frequency current to flow through the treatment target between the bipolar electrodes (21, 22), and outputs heater electric power (P') to the heater (23) thereby to cause the heater (23) to generate heat. In the first phase, the processor (25) starts the output to the bipolar electrodes (21, 22) and detects the initial value (Ze) of the impedance (Z) of the treatment target. In the second phase immediately after the first phase, the processor (25) continues the output to the bipolar electrodes (21, 22) in a manner to modify the treatment target with the high-frequency current applied thereto, and determines whether or not the impedance (Z) has reached the minimum value (Zmin). In the second phase, the processor 25 continues the output to the heater (23) in a manner to modify the treatment target with the heat of the heater (23). Furthermore, the processor (25) acquires parameters, i.e., Ze, Ya, etc. prior to the time when the minimum value (Zmin) of the impedance (Z) related to at least one of the impedance (Z) and the output to the bipolar electrodes (21, 22) is detected. The processor (25) performs at least one of a process of determining whether or not the output to the heater (23) is required and a process of setting a target value, i.e., Tc, Zth, or Ybth, related to the output control process for controlling the output to the heater (23), based on the acquired parameters, i.e., Ze, Ya, etc., in the third phase immediately after the time when the minimum value (Zmin) is detected.

The disclosed technology is not limited to the embodiments described hereinbefore, but various modifications may be made therein without departing from the scope of the invention when it is reduced to practice. The embodiments may be appropriately combined as much as possible, and the combinations offer combined advantages. Furthermore, the embodiments include inventions in various stages, and various inventions can be extracted by appropriately combining a plurality of components that are disclosed.

In sum, one aspect of the disclosed technology is directed to an energy source apparatus of a treatment tool having a heater and bipolar electrodes attached to one another. The energy source apparatus includes an energy output source that outputs high-frequency electric power to the bipolar electrodes so as to cause a high-frequency current to flow through a treatment target between the bipolar electrodes and outputs heater electric power to the heater so as to cause the heater to generate heat. A processor controls the output to the bipolar electrodes and the output to the heater. The processor directs the output to the bipolar electrodes and detects an initial value of the impedance of the treatment target. The processor determines whether or not the impedance has reached a minimum value. The processor retrieves a parameter that is detected before the minimum value of the impedance is detected and the parameter is related to the impedance and/or the output to the bipolar electrodes. The processor performs a first process and/or a second process based on the acquired parameter after the minimum value is detected. The first process determining whether or not the output to the heater is required, the second process setting a target value, the target value is related to an output control process for controlling the output to the heater.

Another aspect of the disclosed technology is directed to a treatment system having a treatment tool and an energy source apparatus. The treatment tool includes a heater and bipolar electrodes to grip a treatment target and the energy source apparatus is used to supply electrical energy to the treatment tool. The energy output source is configured to output high-frequency electric power to the bipolar electrodes so as to cause a high-frequency current to flow through a treatment target between the bipolar electrodes and outputs heater electric power to the heater so as to cause the heater to generate heat. A processor controls the output to the bipolar electrodes and the heater, respectively. The processor directs the output to the bipolar electrodes and detects an initial value of the impedance of the treatment target. Next, the processor determines whether or not the impedance has reached a minimum value and retrieves a parameter that is detected before the minimum value of the impedance is detected. The parameter is related to the impedance and/or the output to the bipolar electrodes. Finally, the processor performs a first process and/or a second process based on the acquired parameter after the minimum value is detected, the first process determines whether or not the output to the heater is required, the second process sets a target value, the target value being related to an output control process for controlling the output to the heater.

A further aspect of the disclosed technology is directed to a method of operating a treatment system having a treatment tool including a heater and bipolar electrodes to grip a treatment target and an energy source apparatus used to supply electrical energy to the treatment tool. The energy source apparatus includes at least one processor to control the output to the bipolar electrodes and the heater, respectively. The at least one processor: directing the output to the bipolar electrodes and detecting an initial value of the impedance of the treatment target; determining whether or not the impedance has reached a minimum value; retrieving a parameter that is detected before the minimum value of the impedance is detected, the parameter being related to the impedance and/or the output to the bipolar electrodes; and performing a first process and/or a second process based on the acquired parameter after the minimum value is detected, the first process determining whether or not the output to the heater is required, the second process setting a target value, the target value being related to an output control process for controlling the output to the heater.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An energy source apparatus of a treatment tool having a heater and bipolar electrodes, the energy source apparatus comprising:
   an energy output source that outputs high-frequency electric power to the bipolar electrodes so as to cause a high-frequency current to flow through a treatment target between the bipolar electrodes, and outputs heater electric power to the heater so as to cause the heater to generate heat; and
   a processor controls the output to the bipolar electrodes and the output to the heater, wherein
   the processor
      directs the output to the bipolar electrodes and detects an initial value of the impedance of the treatment target,
      determines whether or not the impedance has reached a minimum value,
      retrieves a parameter that is detected before the minimum value of the impedance is detected, the parameter being related to the impedance and/or the output to the bipolar electrodes,
      performs a first process and/or a second process based on the retrieved parameter after the minimum value is detected, the first process determines whether or not the output to the heater is required, the second process sets a target value, wherein the target value is related to an output control process for controlling the output to the heater,
      controls the output successively in a first phase, a second phase, and a third phase,
      detects the initial value of the impedance in the first phase,
      proceeds with the output to the bipolar electrodes in a manner to modify the treatment target with the high-frequency current applied thereto, determines whether or not the impedance has reached the minimum value, and applies the output to the heater in a manner to modify the treatment target with the heat of the heater, in the second phase, and performs the first process and/or the second process in the third phase,
      determines a tissue volume of the treatment target based on the parameter, and
      if the processor determines that the tissue volume is smaller than a reference value, then the processor stops the output to the heater or sets a second target temperature lower than a first target temperature as the target value, and performs the output control process on the output to the heater so as to lower the heater temperature to the set second target temperature and to keep the temperature of the heater at the second target temperature, in the third phase.

2. The energy source apparatus of claim 1, wherein the processor sets the first target temperature for the heater in a range of equal or greater than 60° C. to equal or less than 100° C., and performs the output control process on the output to the heater to cause the heater to reach the set first target temperature and to keep the heater at the first target temperature in the second phase.

3. The energy source apparatus of claim 2, wherein the processor increases the output to the heater from the third phase and switches to a fourth phase when
   (i) an impedance in the third phase or
   (ii) an elapsed time from an outset of the third phase is equal to or larger than a threshold value.

4. The energy source apparatus of claim 3, wherein the processor performs the output control process on the output to the heater to increase the heater temperature in the fourth phase to a temperature higher than the first target temperature in the second phase.

5. The energy source apparatus of claim 4, wherein the processor performs the output control process on the output to the heater to increase the heater temperature to 200° C. or higher in the fourth phase.

6. The energy source apparatus of claim 1, wherein the processor detects at least one of the initial value of the impedance and a duration time of the second phase as the parameter, and
the processor sets the target value in the third phase based on the initial value of the impedance and/or the duration time of the second phase that has been detected.

7. The energy source apparatus of claim 6, wherein with respect to the output control process for controlling the output to the heater, the smaller the initial value of the impedance, the processor increases a target temperature for the heater as the target value, and the longer the duration time of the second phase, the processor sets the target temperature for the heater as the target value to a higher value.

8. The energy source apparatus of claim 1, wherein the processor sets at least one of a target temperature for the heater and a threshold value used in determining whether to finish the third phase, as the target value in the third phase, based on the parameter.

9. A treatment system comprising:
a treatment tool having a heater and bipolar electrodes to grip a treatment target; and
an energy source apparatus used to supply electrical energy to the treatment tool wherein
the energy source apparatus configured to output high-frequency electric power to the bipolar electrodes so as to cause a high-frequency current to flow through a treatment target between the bipolar electrodes, and outputs heater electric power to the heater so as to cause the heater to generate heat; and
a processor controls the output to the bipolar electrodes and the heater, respectively, wherein
the processor
   directs the output to the bipolar electrodes and detects an initial value of the impedance of the treatment target,
   determines whether or not the impedance has reached a minimum value, retrieves a parameter that is detected before the minimum value of the impedance is detected, the parameter being related to the impedance and/or the output to the bipolar electrodes, performs a first process and/or a second process based on the acquired parameter after the minimum value is detected, the first process determines whether or not the output to the heater is required, the second process sets a target value, the target value being related to an output control process for controlling the output to the heater, controls the output successively in respective first, second, and a third phases, detects the initial value of the impedance in the first phase, proceeds with the output to the bipolar electrodes in a manner to modify the treatment target with the high-frequency current applied thereto, determines whether or not the impedance has reached the minimum value, and applies the output to the heater in a manner to modify the treatment target with the heat of the heater, in the second phase, performs the first process and/or the second process in the third phase, determines a tissue volume of the treatment target based on the parameter, and if the processor determines that the tissue volume is smaller than a reference value, then the processor stops the output to the heater or sets a second target temperature lower than a first target temperature as the target value, and performs the output control process on the output to the heater so as to lower the heater temperature to the set second target temperature and to keep the temperature of the heater at the second target temperature, in the third phase.

10. The treatment system of claim 9, wherein the processor detects at least one of the initial value of the impedance and a duration time of the second phase as the parameter, and the processor sets the target value in the third phase based on the initial value of the impedance and/or the duration time of the second phase that has been detected.

11. The treatment system of claim 10, wherein with respect to the output control process for controlling the output to the heater, the smaller the initial value of the impedance, the processor increases a target temperature for the heater as the target value, and the longer the duration time of the second phase, the processor sets the target temperature for the heater as the target value to a higher value.

12. The treatment system of claim 9, wherein the processor sets at least one of a target temperature for the heater and a threshold value used in determining whether to finish the third phase, as the target value in the third phase, based on the parameter.

13. A method of operating a treatment system having a treatment tool including a heater and bipolar electrodes to grip a treatment target and an energy source apparatus used to supply electrical energy to the treatment tool, the energy source apparatus comprising at least one processor to control the output to the bipolar electrodes and the heater, respectively, wherein the at least one processor:

directs the output to the bipolar electrodes and detecting an initial value of the impedance of the treatment target;

determines whether or not the impedance has reached a minimum value;

retrieves a parameter that is detected before the minimum value of the impedance is detected, the parameter being related to the impedance and/or the output to the bipolar electrodes;

performs a first process and/or a second process based on the acquired parameter after the minimum value is detected, the first process determining whether or not the output to the heater is required, the second process setting a target value, the target value being related to an output control process for controlling the output to the heater;

controls the output successively in respective first, second, and a third phases;

detects the initial value of the impedance in the first phase;

proceeds with the output to the bipolar electrodes in a manner to modify the treatment target with the high-frequency current applied thereto, determines whether or not the impedance has reached the minimum value, and applies the output to the heater in a manner to modify the treatment target with the heat of the heater, in the second phase;

performs the first process and/or the second process in the third phase;

determines a tissue volume of the treatment target based on the parameter; and if the processor determines that the tissue volume is smaller than a reference value, then the processor stops the output to the heater or sets a second target temperature lower than a first target temperature as the target value, and performs the output control process on the output to the heater so as to lower the heater temperature to the set second target temperature and to keep the temperature of the heater at the second target temperature, in the third phase.

* * * * *